United States Patent
Zuardy et al.

(10) Patent No.: US 9,371,128 B2
(45) Date of Patent: Jun. 21, 2016

(54) STRUCTURAL COMPONENT COMPRISING AT LEAST ONE MAIN-LOAD-BEARING COVERING SHELL AND A CARRIER STRUCTURE FOR FIXING THE MAIN-LOAD-BEARING COVERING SHELL, AND FLOW BODY COMPRISING SUCH A STRUCTURAL COMPONENT

(71) Applicant: Airbus Operations GmbH, Hamburg (DE)

(72) Inventors: Ichwan Zuardy, Hamburg (DE); Pierre Zahlen, Stade (DE); Axel Siegfried Herrmann, Stade (DE)

(73) Assignee: Airbus Operations GmbH, Hamburg (DE)

( * ) Notice: Subject to any disclaimer, the term of this patent is extended or adjusted under 35 U.S.C. 154(b) by 0 days.

(21) Appl. No.: 13/742,919

(22) Filed: Jan. 16, 2013

(65) Prior Publication Data

US 2014/0050884 A1 Feb. 20, 2014

Related U.S. Application Data

(63) Continuation of application No. PCT/EP2011/003642, filed on Jul. 20, 2011.

(30) Foreign Application Priority Data

| Jul. 20, 2010 | (DE) | 10 2010 027 695 |
| Jul. 20, 2010 | (DE) | 10 2010 027 696 |
| Jul. 20, 2010 | (DE) | 10 2010 031 688 |
| Jul. 20, 2010 | (DE) | 10 2010 031 690 |

(51) Int. Cl.
*B64C 1/12* (2006.01)
*B64C 3/20* (2006.01)
(Continued)

(52) U.S. Cl.
CPC ... *B64C 1/12* (2013.01); *B32B 3/08* (2013.01); *B32B 3/28* (2013.01); *B32B 3/30* (2013.01);
(Continued)

(58) Field of Classification Search
CPC .............. B64C 1/12; B64C 3/26; B64C 3/20; B32B 2605/18; B32B 3/02; B32B 3/06; B32B 3/08; Y10T 428/249923
USPC ........................................................ 428/119
See application file for complete search history.

(56) References Cited

U.S. PATENT DOCUMENTS

| 3,803,485 A | 4/1974 | Crites et al. |
| 3,837,985 A | 9/1974 | Chase |

(Continued)

FOREIGN PATENT DOCUMENTS

| CA | 2 330 275 A1 | 11/1999 |
| CN | 201 254 685 | 6/2009 |

(Continued)

OTHER PUBLICATIONS

Berg, DE2132446 English Translation, Jan. 18, 1973.*

(Continued)

*Primary Examiner* — Aaron Austin
*Assistant Examiner* — Jasper Saberi
(74) *Attorney, Agent, or Firm* — Jenkins, Wilson, Taylor & Hunt, P.A.

(57) ABSTRACT

Structural component including at least one covering shell and a carrier structure, the covering shell designed in the form of a sandwich and formed by an inner skin section, an outer skin section and a shear-load absorbing core layer disposed between the two sections and connecting the inner and the outer skin sections to one another in a planar manner. The carrier structure is formed by at least one panel-shaped connecting part extending between and transversely to the inner and outer skin sections and connected along a reference longitudinal direction to the covering shell. The connecting part is located outside the carrier structure and fastened to the inner skin section resting thereon in a planar manner, wherein at least one profiled support extending along the reference longitudinal direction is provided in the covering shell in order to form a reinforcing section in the connecting region of the panel-shaped connecting part.

22 Claims, 8 Drawing Sheets

(51) Int. Cl.

| | | |
|---|---|---|
| *B64C 3/26* | (2006.01) | |
| *B64D 45/00* | (2006.01) | |
| *B32B 5/18* | (2006.01) | |
| *B32B 3/08* | (2006.01) | |
| *B32B 3/28* | (2006.01) | |
| *B32B 3/30* | (2006.01) | |
| *B32B 7/04* | (2006.01) | |
| *G01N 19/08* | (2006.01) | |
| *B32B 3/06* | (2006.01) | |
| *B32B 3/02* | (2006.01) | |

(52) U.S. Cl.
CPC ... *B32B 5/18* (2013.01); *B32B 7/04* (2013.01); *B64C 3/20* (2013.01); *B64C 3/26* (2013.01); *B64D 45/00* (2013.01); *G01N 19/08* (2013.01); *B32B 3/02* (2013.01); *B32B 3/06* (2013.01); *B32B 2605/18* (2013.01); *B64D 2045/0085* (2013.01); *Y10T 428/239* (2015.01); *Y10T 428/24* (2015.01); *Y10T 428/24322* (2015.01); *Y10T 428/249923* (2015.04)

(56) References Cited

U.S. PATENT DOCUMENTS

| | | | | |
|---|---|---|---|---|
| 4,350,728 | A | * | 9/1982 | Huang ............... B29C 65/564 244/123.1 |
| 4,484,132 | A | | 11/1984 | Crites |
| 4,584,230 | A | | 4/1986 | Saegusa |
| 4,910,065 | A | | 3/1990 | McKinney |
| 5,736,222 | A | | 4/1998 | Childress |
| 5,827,383 | A | * | 10/1998 | Campbell et al. ............ 156/73.1 |
| 5,869,165 | A | | 2/1999 | Rorabaugh |
| 5,935,680 | A | * | 8/1999 | Childress ..................... 428/119 |
| 5,958,550 | A | | 9/1999 | Childress |
| 5,969,260 | A | | 10/1999 | Belk |
| 6,178,825 | B1 | | 1/2001 | Chang et al. |
| 6,291,049 | B1 | | 9/2001 | Kunkel |
| 2004/0055248 | A1 | * | 3/2004 | Grillos ........................ 52/783.1 |
| 2005/0208274 | A1 | | 9/2005 | Endres et al. |
| 2006/0188696 | A1 | | 8/2006 | Grose |
| 2007/0062300 | A1 | | 3/2007 | Dorfman |
| 2008/0128552 | A1 | * | 6/2008 | Namaizawa et al. ...... 244/123.1 |
| 2008/0138584 | A1 | | 6/2008 | Grose et al. |
| 2008/0176024 | A1 | | 7/2008 | Weber |
| 2009/0020212 | A1 | | 1/2009 | Cacace |
| 2009/0035510 | A1 | | 2/2009 | Chakrabarti |
| 2010/0092300 | A1 | | 4/2010 | Jensen |
| 2010/0151189 | A1 | * | 6/2010 | Chakrabarti ................. 428/119 |
| 2013/0266756 | A1 | | 10/2013 | Zuardy et al. |
| 2013/0273301 | A1 | | 10/2013 | Zuardy et al. |
| 2014/0000381 | A1 | | 1/2014 | Zuardy et al. |

FOREIGN PATENT DOCUMENTS

| | | |
|---|---|---|
| DE | 213 2446 | 1/1973 |
| DE | 19945557 | 3/2001 |
| DE | 10 2006 056568 | 6/2008 |
| DE | 10 2010 026 696.0 | 1/2010 |
| DE | 10 2010 027 695.2 | 1/2012 |
| DE | 10 2010 031 688.1 | 1/2012 |
| DE | 10 2010 031 690.3 | 1/2012 |
| EP | 0891859 | 1/1999 |
| EP | 0 904 929 B1 | 11/2002 |
| GB | 2 029 019 | 3/1980 |
| WO | WO 03-031159 | 4/2003 |
| WO | WO 2008-144023 | 11/2008 |
| WO | WO 2010-010382 A2 | 1/2010 |
| WO | WO 2012-010304 | 1/2012 |
| WO | WO 2012-010305 | 1/2012 |
| WO | WO 2012-010306 | 1/2012 |
| WO | WO 2012-010307 | 1/2012 |

OTHER PUBLICATIONS

Zuardy et al, DE102010031690_English, Jan. 26, 2012.*
Chinese Search Report for Application No. 201180045269.6 dated Sep. 24, 2014.
Chinese Office Action for Application No. 201180045269.6 dated Oct. 8, 2014.
Chinese Office Action for Application No. 201180045272.8 dated Sep. 2, 2014.
Non-Final Office Action for U.S. Appl. No. 13/743,739 dated Feb. 25, 2015.
Restriction Requirement for U.S. Appl. No. 13/743,739 dated Dec. 12, 2014.
Chinese Search Report for Application No. 201180045272.8 dated Aug. 25, 2014.
Restriction Requirement for U.S. Appl. No. 13/743,767 dated May 13, 2015.
Chinese Office Action for Application No. 201180045258.8 dated Mar. 30, 2015.
Final Office Action for U.S. Appl. No. 13/743,739 dated Jun. 3, 2015.
Non-Final Office Action for U.S. Appl. No. 13/743,767 dated Aug. 3, 2015.
Chinese Office Action for Application No. 201180045272.8 dated May 6, 2015.
Chinese Office Action for Application No. 201180045300.6 dated Aug. 11, 2014.
Chinese Office Action for Application No. 201180045258.8 dated Aug. 19, 2014.
German Office Action for Application No. 10 2010 031 690.3 dated May 6, 2014.
Final Office Action for U.S. Appl. No. 13/742,679 dated Aug. 29, 2014.
Non-Final Office Action for U.S. Appl. No. 13/742,679 dated Jan. 16, 2014.
International Preliminary Report on Patentability for International Application No. PCT/EP2011/003641 dated Jan. 22, 2013.
International Preliminary Report on Patentability for International Application No. PCT/EP2011/003642 dated Jan. 22, 2013.
International Preliminary Report on Patentability for International Application No. PCT/EP2011/003643 dated Jan. 22, 2013.
International Preliminary Report on Patentability for International Application No. PCT/EP2011/003644 dated Jan. 22, 2013.
International Search Report for Application No. PCT/EP2011/003641 dated Oct. 20, 2011.
International Search Report for Application No. PCT/EP2011/003642 dated Oct. 24, 2011.
International Search Report for Application No. PCT/EP2011/003643 dated Oct. 26, 2011.
International Search Report for Application No. PCT/EP2011/003644 dated Oct. 31, 2011.
Chinese Office Action for Application No. 201180045269.6 dated Aug. 27, 2015.

* cited by examiner

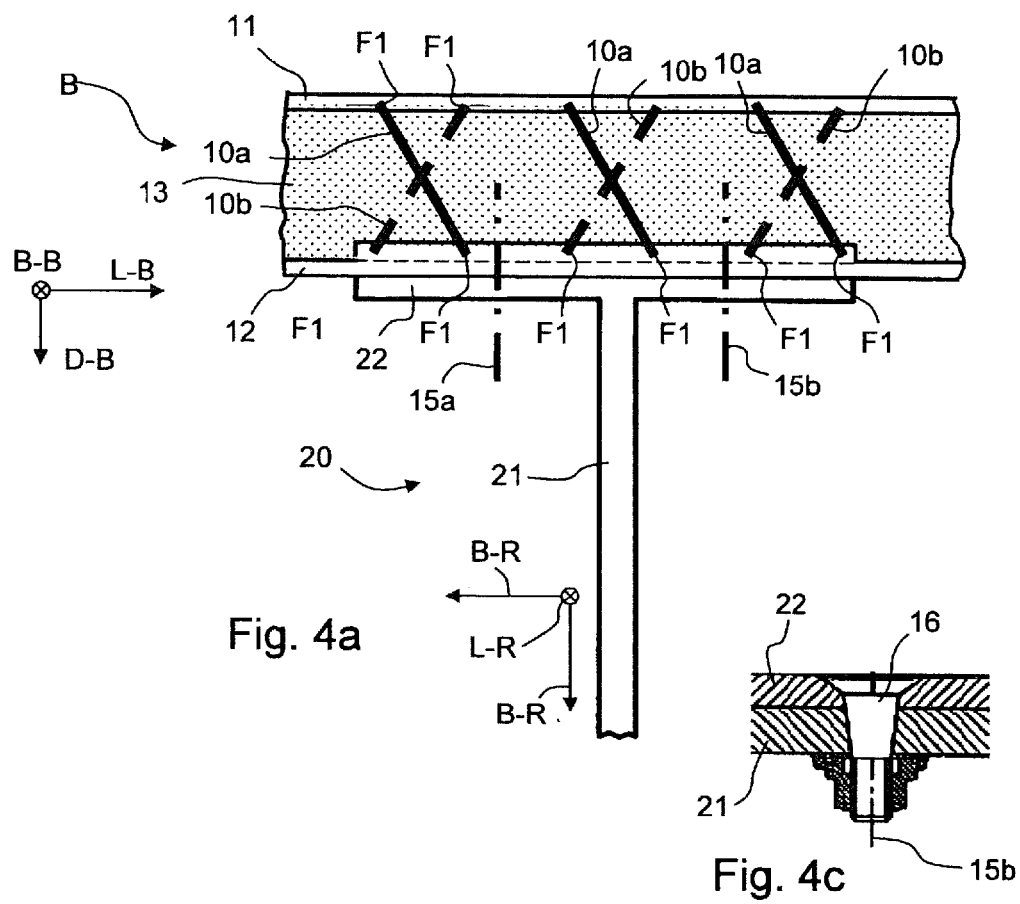
Fig. 4a
Fig. 4c
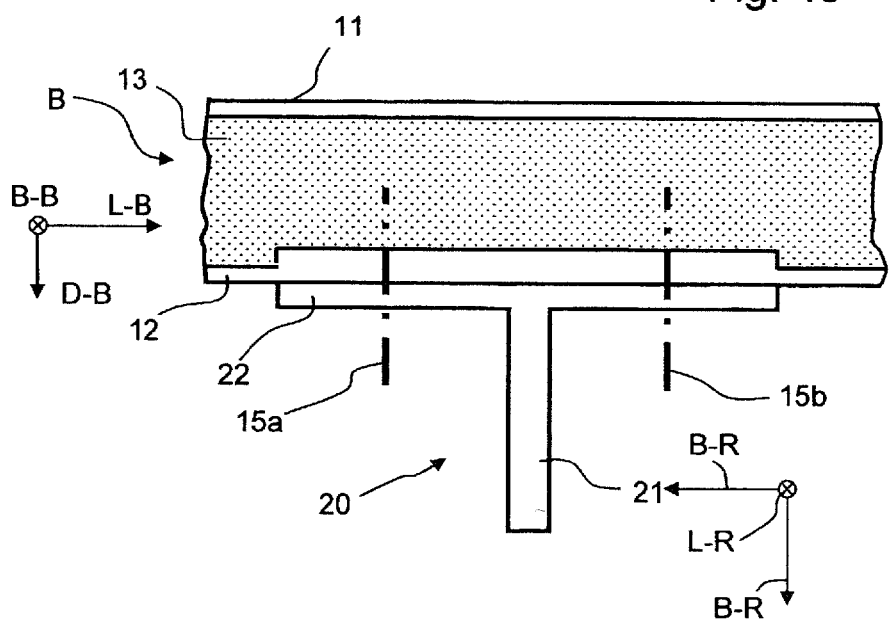
Fig. 4b

STRUCTURAL COMPONENT COMPRISING AT LEAST ONE MAIN-LOAD-BEARING COVERING SHELL AND A CARRIER STRUCTURE FOR FIXING THE MAIN-LOAD-BEARING COVERING SHELL, AND FLOW BODY COMPRISING SUCH A STRUCTURAL COMPONENT

CROSS-REFERENCE TO RELATED APPLICATIONS

This patent application is a continuation of and claims priority to PCT application No. PCT/EP2011/003642, filed Jul. 20, 2011, which asserts the date of filing of the German patent applications DE 10 2010 027 696.0, DE 10 2010 027 695.2, DE 10 2010 031 688.1, DE 10 2010 031 690.3, all filed on Jul. 20, 2010. With the above reference the disclosures of these patent applications are contained in the present patent application.

TECHNICAL FIELD

The invention relates to a structural component with at least one main-load bearing skin shell and a support structure for connecting the main-load bearing skin shell and flow body with such a structural component.

BACKGROUND

From U.S. Pat. No. 6,291,049 a skin plate in a sandwich construction is known into which pin-shaped reinforcement elements for stabilising the skin plate have been inserted.

SUMMARY

It is an object of the invention to provide a structural component with at least one main-load bearing skin shell and a support structure for connecting the main-load bearing skin shell and flow body with such a structural component, which is designed so as to be damage-tolerant and which, at the same time, is suitable for absorbing considerable strain while being of a lightweight construction.

These objects are met by the characteristics of the independent claims. Further embodiments are stated in the related subordinate claims.

According to one aspect of the invention, a structural component with at least one main-load bearing skin shell and a support structure for fixing the skin shell ist provided. The skin shell is constructed as a sandwich component and comprises an inner skin section, an outer skin section and a shear-force-absorbing core layer which is situated between the aforesaid and which two-dimensionally interconnects the inner and the outer skin sections. Further, the support structure is formed of a plate-shaped connection piece which extends between and across these and is connected with the skin shell along a reference longitudinal direction, wherein the plate-shaped connection piece is disposed at the support structure outside the support structure for supporting the skin shell in a laminar manner. In particular, it is provided that in the skin shell at least one profile carrier is disposed which extends along the reference longitudinal direction for forming reinforcement section in the connecting region of the plate-shaped connection piece, wherein the at least one profile carrier is connected to the inner skin section and outer skin section for stabilization of skin shell in the case of a damage of the same and which thereby supports the inner skin section and outer skin section with regard to each other from the outside. In particular, it is provided that the connection piece is disposed at the support structure outside the support structure, in the thickness direction of the skin shell, for supporting the skin shell and is connected to the inner skin section adjacent to the inner skin section. In this regard, it can in particular be provided, that the at least one profile carrier is disposed within the connecting region, when seen in a top view onto the two-dimensional extension of the skin shell. Alternatively or additionally it can be provided that in the connection region of the plate-shaped connection component along the reference direction or the longitudinal direction of the rib arrangement a multitude of reinforcement components are integrated.

The solution according to the invention with attachment of the connection component to the skin shell in such a manner that the connection component is situated outside the skin shell and two-dimensionally rests against the inner skin section provides an advantage in that the inner skin section and the outer skin section remain intact. This makes it possible to manufacture the skin shell with continuous inner and outer skin sections, which in turn makes it possible to manufacture the skin shell with the use of a resin infusion process or wet process (liquid composite moulding process).

In this arrangement the connection component for the attachment of the aforesaid of the skin shell can be two-dimensionally bonded to the inner skin section so that, due to the adhesive force two-dimensionally provided by the adhesive, the connection component is held to the skin shell. In addition or as an alternative to this, the connection component with the skin shell can be connected to the inner skin section by means of fasteners such as, in particular, rivets (blind rivets, lock bolts, etc.) which, in particular, can be affixed so as to be regularly spaced apart from each other in at least two rows that extend so as to be parallel along each other or to each other.

In the connection region it can, in particular, be provided that the inner skin section, against which the connection component rests, comprises a greater material thickness than the inner skin section laterally of the connection region. According to one embodiment of the invention, this thickening in terms of its two-dimensional extent can be in a region that deviates by a maximum of ten times the thickness of the skin shell from the edge contour of the connection region. This increase in thickness can be implemented by arranging further layers in this two-dimensionally extending region on the core layer and/or on the surface of the inner skin section, which surface faces the outside of the skin shell.

According to one embodiment of the structural component according to the invention, it is provided that in the connection region of the plate-shaped connection component along the reference longitudinal direction a multitude of reinforcement components are integrated.

According to one embodiment of the structural component according to the invention, it is provided that at least some of the reinforcement components are arranged in the core layer in such a manner that in each case their ends at least in part project through the inner skin section and/or the outer skin section, wherein, in particular, in each case the inner skin section and the outer skin section comprise several layers, and at least part of the reinforcement components penetrate at least a first layer.

Generally speaking, in this document the term "skin shell" refers to a shell component that according to the invention is designed as a sandwich shell and that can be curved or not curved.

According to a further aspect of the invention, a structural component with at least one main-load bearing skin shell and a support structure for the attachment of the skin shell is provided, wherein the skin shell is formed as a sandwich comprising an inner skin section, an outer skin section and a shear-force-absorbing core layer situated between the aforesaid, which core layer two-dimensionally interconnects the inner and the outer skin sections, wherein the support structure comprises at least one plate-shaped connection component that extends between and across the aforesaid and that is connected to the skin shell along a reference longitudinal direction, which connection component for supporting the skin shell on the support structure is situated outside the support structure and, two-dimensionally resting on the inner skin section, is affixed to said skin section. In this arrangement in the connection region of the plate-shaped connection component a multitude of reinforcement components are integrated along the reference longitudinal direction. Moreover, at least some of the reinforcement components are arranged in the core layer in such a manner that in each case their ends at least in part project through the inner skin section and/or through the outer skin section.

The solution according to the invention with attachment of the connection component to the skin shell in such a manner that the connection component is situated outside the skin shell and two-dimensionally rests against the inner skin section provides an advantage in that the inner skin section and the outer skin section remain intact. This makes it possible to manufacture the skin shell with continuous inner and outer skin sections. This in turn makes it possible to manufacture the skin shell with the use of a resin infusion process or wet process (liquid composite moulding process).

In this arrangement the connection component for the attachment of the said connection component to the skin shell can be two-dimensionally bonded to the inner skin section. In addition or as an alternative to this, the connection component with the skin shell can be connected to the inner skin section by means of fasteners such as, in particular, rivets which, in particular, can be affixed so as to be regularly spaced apart from each other in at least two rows that extend so as to be parallel along each other or to each other.

In the connection region it can, in particular, be provided that the inner skin section, against which the connection component rests, comprises a greater material thickness than the inner skin section laterally of the connection region. According to one embodiment of the invention, this thickening in terms of its two-dimensional extent can be in a region that deviates by a maximum of ten times the thickness of the skin shell from the edge contour of the connection region. This increase in thickness can be implemented by arranging further layers in this two-dimensionally extending region on the core layer and/or on the surface of the inner skin section, which surface faces the outside of the skin shell.

According to one embodiment of the structural component according to the invention, it is provided that in each case the inner skin section and the outer skin section comprise several layers, wherein the reinforcement components penetrate at least one first layer of the inner skin section and of the outer skin section.

According to one embodiment of the structural component according to the invention, it is provided that in the skin shell at least one profile carrier, which extends along the reference longitudinal direction, is arranged to form a reinforcement section in the connection region of the plate-shaped connection component, which profile carrier is connected to the inner skin section and the outer skin section for stabilising the skin shell in the case of damage of said skin shell, thus providing mutual support from the outside. In the embodiments according to the invention, the support structure can particularly comprise at least one rib arrangement which extends between and across the same and is connected with the skin shell along a longitudinal direction of the rib arrangement for supporting the skin shell to the support structure in a laminar manner. The support structure can comprise: the plate-shaped connection component which extends in the longitudinal direction of the rib arrangement and which is formed as a flange component, which is connected with a connecting region of the inner skin section of the skin shell, e.g. in a laminar manner, and a rib which follows on from the flange component and protrudes from the skin shell in a reference longitudinal direction of the rib arrangement. In this regard it can be provided that reinforcement components or reinforcement devices are integrated in an intermediate region along the longitudinal direction of the rib arrangement and along a lateral end of the skin shell section.

According to an embodiment of the invention the intermediate region for the arrangement of the reinforcement devices extends in an area from an edge of the end of the core layer to a distance of a maximum of ten times the thickness of the skin shell at the edge of the end of the core layer.

According to an embodiment of the invention it is provided that several reinforcement components are disposed beside each other in an area across the longitudinal direction of the rib arrangement and in that several reinforcement components are disposed along reinforcement profiles and along the longitudinal direction of the rib arrangement. Particularly it can be provided that only between the two outmost carriers or the three outmost carriers several reinforcement components or reinforcement devices are disposed.

Further it can be provided that at least one reinforcement profile carrier is provided which is formed of two profile plates, one of which is connected to the inner skin section and the respective other one is connected to the outer skin section, and a support rib that connects the aforesaid and that its profile cross section is a double-T profile cross section. At edge portions which define the connecting region in each case two reinforcement profile carriers can be disposed side by side, between which reinforcement components are inserted in the core layer. Particularly, reinforcement components can be inserted such that the ends of a respective one of the reinforcement components at least partially penetrate a profile plate being disposed at the inner skin section and a profile plate being disposed at the outer skin section, the profile plates being part of reinforcement profile carriers which lay side by side to each other. In this regard, the reinforcement components can have, in respective pairs of the aforesaid, an X-wise orientation.

Alternatively or additionally it can be provided that at least one reinforcement profile carrier is provided, which is formed of two profile plates and two support ribs, wherein one of the two profile plates is connected to the inner skin section and the other one of the two profile plates is connected to the outer skin section, in that the profile cross section of the reinforcement profile carrier is a box-shaped profile cross section. The reinforcement components can be inserted such that the ends of a respective one of the reinforcement components at least partially penetrate a profile plate being disposed at the inner skin section and a profile plate being disposed at the outer skin section, the profile plates being part of the same reinforcement profile carrier. In this regard, the reinforcement components can have, in respective pairs of the aforesaid, an X-wise orientation.

According to an embodiment of the invention it is provided that along at least one reinforcement profile carrier in the longitudinal direction of the rib arrangement several reinforcement components are integrated which project through at least 85% of the shear-force-absorbing core layer in the latter's thickness direction in order to improve the crack resistance of the skin shell in the outer edge section.

According to an embodiment of the invention it is provided that at least a part of the reinforcement components are disposed in the core layer such that the ends thereof penetrate at least partially the inner skin section and/or the outer skin section. In this regard it can particularly be provided that in each case the inner skin section and the outer skin section comprise several layers, wherein the reinforcement components penetrate at least one first layer of the inner skin section and of the outer skin section.

According to the invention a main-load bearing skin shell for a structural component is provided. The skin shell is designed as a sandwich component and comprises an inner skin section, an outer skin section and a shear-force-absorbing core layer, situated between the aforesaid, which skin section two-dimensionally interconnects the inner and the outer skin sections. According to the invention, for influencing of shear stresses in the core layer, the skin shell can comprise a plurality of reinforcement devices which are disposed in an intermediate area, wherein the reinforcement devices are formed of a combination of at least two reinforcement parts which are disposed in a contiguous spatial part within the skin shell, wherein the reinforcement components are arranged, in the longitudinal direction of the intermediate region, one behind the other, wherein, with the combination of the reinforcement parts, within a deviation of a maximum of 10 degrees the reinforcement devices in each case have the same orientation relative to the thickness direction of the skin shell, and the alignment of the reinforcement components relative to the further coordinate directions of the skin shell is cyclically provided.

In this regard, the alignment of the reinforcement components can, in particular, be provided in such a manner that the angle between the longitudinal direction of the respective reinforcement component and the thickness direction of the skin shell at this position is within a range of between 45 degrees and 10 degrees.

In the embodiments according to the invention, in which reinforcement components are provided, it can, in principle, be provided that the reinforcement components, or part of the reinforcement components, in the skin shell are in each case arranged, as reinforcement components, in groups of reinforcement components, wherein the volume components along a reference longitudinal direction or the longitudinal direction of the ribs are arranged one behind the other, wherein each group of a volume component in each case comprises a combination of at least two reinforcement components whose alignments in each case deviate by a maximum of 30 degrees from the thickness direction of the skin shell, and which reinforcement components are arranged in a regular or irregular manner around a centre axis of the volume component. The volume component is a fictitious volume component of the skin shell, selected to illustrate the arrangement of reinforcement components, which volume component extents over the entire thickness of the aforesaid and is, in particular, in the shape of a rectangular parallelepiped. In this case, in particular, the centre axis of the volume component can be the centre axis or symmetry axis that extends in the thickness direction of the skin shell and that connects the cross-sectional area centres of gravity of the rectangular parallelepiped.

According to an embodiment of the invention it is provided that the reinforcement components, in a reference longitudinal direction and in particular in a longitudinal direction of the rib arrangement, are arranged one behind the other, each comprising pairs of reinforcement components, wherein the reinforcement components of each pair of reinforcement components, when viewed in the direction of the longitudinal extension of the skin shell, are oriented to each other in such a manner that the reinforcement components form a reinforcement device that is X-shaped. In this regard, the arrangement of reinforcement devices can be disposed in an longitudinally extending reinforcement area which extends in its longitudinal direction along the reference longitudinal direction and in particular in the longitudinal direction of the rib arrangement or along a connecting area which is provided for fixing a rib arrangement or a carrier component, wherein the width of the reinforcement area amounts to a maximum of ten times the thickness of the skin shell in this area.

The reinforcement components can be designed so as to be at least in part pin-shaped. As an alternative or in addition, reinforcement components can comprise a plate-shaped design. In this arrangement the plate-shaped reinforcement components of a reinforcement device can be arranged so as to engage each other.

According to a further aspect of the invention, a structural component with at least one main-load bearing or main-bearing skin shell and a support structure for the attachment of the skin shell are provided. The skin shell is designed as a sandwich comprising an inner skin section, an outer skin section and a shear-force-absorbing core layer situated between the aforesaid, which core layer, in particular, interconnects the inner skin section and the outer skin section in a laminar manner. The support structure comprises at least two support components, each extending along a longitudinal direction of the structural component, and at least one rib arrangement, extending between and across said support components, and along their longitudinal direction connected to the skin shell, for two-dimensionally supporting the skin shell on the support structure. The rib arrangement comprises: a rib protruding from the skin shell in its transverse direction, and a flange component, following on from the above, which flange component along the longitudinal direction of the rib arrangement is two-dimensionally connected to the skin shell. According to the invention, in the skin shell, along a skin shell section that extends across the longitudinal direction of the rib arrangement, reinforcement profiles are arranged, which reinforcement profiles or reinforcement devices interconnect from the outside the flange part and the outer skin section for stabilising the skin shell when the latter is damaged. Furthermore, on two intermediate regions or reinforcement regions, which extend in the longitudinal direction of the rib arrangement and along the lateral ends of the skin shell section, reinforcement devices are integrated. These are particularly designed as reinforcement parts which penetrate the core layer, wherein the reinforcement devices at least in some sections are arranged along the longitudinal direction of the rib arrangement, i.e. situated one behind the other in the longitudinal direction of the rib arrangement.

According to an embodiment, the skin shell, for influencing of shear stresses in the core layer, can comprise a plurality of reinforcement devices disposed in the intermediate areas, which in each case are formed of a combination of at least two reinforcement components which are disposed in a contiguous spatial part within the skin shell. In this arrangement, the reinforcement devices are arranged, in the longitudinal direction of the intermediate region one behind the other. With the combination of the reinforcement components, within a deviation of a maximum of 10 degrees, the reinforcement devices in each case have the same orientation relative to the thickness direction of the skin shell, and the alignment of the reinforcement components relative to the further coordinate directions of the skin shell is cyclically provided.

Further in this regard it can be, in particular, provided that the orientation of the reinforcement components is within an angular range of between 45 degrees and 10 degrees, wherein the amount of these angles is defined by the size of the angle between the longitudinal direction of the respective reinforcement component and the thickness direction of the skin shell at this position. The reinforcement devices can be disposed one behind each other when seen in the longitudinal direction of the rib arrangement and can be formed of, in each case, a pair of reinforcements components, wherein, wherein the reinforcement components of each pair of reinforcement components are oriented to each other in such a manner that the reinforcement components relative to each other form a reinforcement device that is X-shaped when viewed in a longitudinal extension of the skin shell. The reinforcement components can be of a pin-shaped design. Furthermore it can be provided that as reinforcement devices reinforcement components are applied which are, at least partially, of a plate-shaped design and extend in each case in the longitudinal direction o the rib arrangement. In this arrangement it can, in particular, be provided that in each case at least two plate-shaped reinforcement components, which are X-shaped when viewed in the longitudinal direction of the rib arrangement are arranged so as to engage each other.

According to an embodiment of the invention a reinforcement device can be formed, in each case, of a pair of reinforcement components, wherein the reinforcement components of each pair of reinforcement components are oriented with regard to each other such that the reinforcement components form a x-shaped reinforcement device when viewed in a longitudinal extension of the skin shell.

The reinforcement components can at least be of a pin-shaped design and/or at least at an end be of a needle-shaped design. Alternatively or additionally, reinforcement components can be of a plate-shaped design. Further, at least one end of reinforcement components can in each case comprise a foot-like widened part. In this arrangement, the reinforcement components which are of plate-shaped design can be arranged so as to engage each other.

The shear-force-absorbing core layer can comprise the core-layer reinforcement region which in some sections in directions across the longitudinal extension of the shear-force-absorbing core layer extends through said core layer, wherein the reinforcement region comprises a material that provides at least twice the stiffness of the shear-force-absorbing core layer. The core-layer reinforcement region can, in particular, comprise a resin, for example an epoxy resin. The structural component can be designed in such a manner that in each case several of the reinforcement components project through the core layer reinforcement region.

According to the invention, a flow body with a structural component is also provided, wherein the structural component is a main-load bearing structural component designed according to any one of the above-mentioned embodiments.

According to a further aspect of the invention, a main-load bearing skin shell for a structural component of a flow body is provided, wherein the skin shell is constructed as a sandwich and comprises an inner skin section, an outer skin section and a shear-force-absorbing core layer situated between the aforesaid, wherein the shear-force-absorbing core layer interconnects the inner and the outer skin sections in a laminar manner, wherein the shear-force-absorbing core layer comprises several core-layer sections, arranged one beside the other in the longitudinal extension of the foam layer, which core-layer sections in each case on the contacting sides are interconnected by a core layer reinforcement region that extends across the longitudinal direction of the core layer through said core layer. In this arrangement the core-layer reinforcement region can comprise resin.

According to a further embodiment it is provided that along a surrounding region of the core-layer reinforcement region a multitude of core-layer reinforcement regions are integrated in the shear-force-absorbing core layer of the skin shell reinforcement devices. In this arrangement the surrounding region for the arrangement of the reinforcement devices on both sides of the core-layer reinforcement region can extend a distance of a maximum of double the thickness, of the skin shell at the respective position of the core-layer reinforcement region.

In this arrangement it can, in particular, be provided that the reinforcement devices in the longitudinal direction of the core-layer reinforcement region are arranged one behind the other and in each case are formed of a combination of at least two reinforcement components which in each case with a deviation of a maximum of 10 degrees have the same orientation relative to the thickness direction of the skin shell, and the alignments of the reinforcement components relative to the further coordinate directions of the skin shell are cyclically provided. Further in this regard it can be, in particular, provided that the orientation of the reinforcement components is within an angular range of between 45 degrees and 10 degrees, wherein the amount of these angles is defined by the size of the angle between the longitudinal direction of the respective reinforcement component and the thickness direction of the skin shell at this position.

The reinforcement devices can, in particular, in the longitudinal direction of the core-layer reinforcement region be arranged one behind the other, each comprising a pair of reinforcement components, wherein the reinforcement components of each pair of reinforcement components are oriented to each other in such a manner that the reinforcement components relative to each other form a reinforcement device that is X-shaped when viewed in a longitudinal extension of the skin shell. The reinforcement devices can, at least in part, comprise a pin-shaped design. Furthermore, it can be provided that in each case several of the reinforcement components project through the reinforcement region.

The structural component, provided according to the above-mentioned aspect of the invention, of a flow body with at least one main-load bearing skin shell and a support structure for the attachment of the skin shell and the formation of the skin shell from core-layer sections, which in each case are on abutting sides are interconnected by a core layer reinforcement region, can, in particular, be provided in combination with the use of a rib arrangement in which, along a skin shell section that extends across the longitudinal direction of the rib arrangement, reinforcement profiles are arranged. In this arrangement the arrangement and design of the reinforcement profiles can be designed according to any one of the above-mentioned exemplary embodiments.

According to the invention, furthermore, a flow body with a structural component can be provided, wherein the structural component is designed as a main-bearing structural component according to any one of the above-mentioned exemplary embodiments.

According to the invention, furthermore, a structural component of a flow body with at least one such main-load bearing skin shell described above and a support structure for the attachment of the skin shell is provided. In such a structural component it can be provided that the support structure comprises at least two support components, each extending along a longitudinal direction of the structural component, and at least one rib arrangement, extending between and across said support components, and along their longitudinal direction connected to the skin shell, for two-dimensionally supporting the skin shell on the support structure, and that, in particular, said support structure can comprise the characteristics mentioned herein in this context.

According to the invention, a flow body with a structural component can also be provided, which structural component is a main-load bearing structural component and is designed according to one or several of the above-mentioned characteristics.

In this context the term "flow body" refers to a body around which a current flows, which body thus comprises a flow surface which, in particular, forms a section of the outside of a vehicle subjected to a flow. The flow body can, in particular, be a body subjected to a flow, and thus an aerodynamic body. In this context, generally speaking, an aerodynamic body can be part of a vehicle and, in particular, part of an aircraft. The vehicle can also be an earth-bound vehicle, and thus the aerodynamic body can be a spoiler. Moreover, the flow can be a liquid flow, and the flow body can be a ship's hull or body or part thereof.

According to one exemplary embodiment of the invention, the skin shell according to the invention is a section of the skin of an aircraft component, for example of a rudder of a tail unit and, in particular, of an elevator unit or of a vertical stabiliser and thus of an elevator unit fin or of a vertical stabiliser fin or of an elevator unit rudder or of a vertical stabiliser ruder, of a wing, of a control flap or of a high-lift flap, of a canard or of a fuselage, in other words, generally speaking, of an aerodynamic body. In this context the predetermined maximum force is the impact of a body at a maximum weight at an assumed speed of the aircraft, and thus flow speed. In terms of the skin shell provided according to the invention, damage is admissible that still ensures the airworthiness of the aircraft.

According to the invention, a structural component of a flow body with a skin shell and a skin shell of a flow body are provided, wherein the skin shell is integrated in the structural component in such a manner that said skin shell forms a flow surface and at the same time is a main-load bearing component of the flow body.

According to the invention, a structural component or a skin shell of a structural component of the flow body as a main-load bearing structural part is formed. In this context the term "main-bearing" or "main-load bearing" refers to a structural component or a component thereof, or to a skin shell, which structural component in terms of its load as a result of external forces in the flow body takes up and transfers main loads. Thus the main-load bearing components of the flow body are to be designed to the effect that when assumed external maximum forces occur, said components remain intact as structural components and need to be in a position to continue to transfer minimum loads. To this effect the skin shell provided according to the invention is a "damage-tolerant" part or a "damage-tolerant" component, because when a predetermined external maximum force occurs, damage to the skin shell is tolerated; however, damage must not occur to such an extent that the flow body as a whole could no longer carry out its flow function.

The reinforcement devices provided in the various aspects of the invention and/or in the exemplary embodiments and variants of the invention in the respective skin shell can, generally speaking, be designed according to the exemplary embodiments stated in this document. The respective direction or longitudinal direction, along which the reinforcement devices in the skin shell in the respective application are arranged, depends on the orientation and design of the region of the skin shell, which region is to be reinforced in the respective application case, in this context also referred to as the intermediate region or reinforcement region.

The respective longitudinal direction can, in particular, be the direction of a region by means of which the absorption of shear stress and thus the prevention of crack formation in the core layer can be achieved. In particular, the following can be provided as the respective longitudinal direction or course along which the reinforcement devices are arranged according to the invention: in the case of connecting or affixing the skin shell to a rib arrangement the longitudinal direction of the rib arrangement; in the case of the formation of core-layer sections comprising core-layer reinforcement regions the longitudinal direction or the longitudinal course of the reinforcement regions or of a section of them; in the formation of the skin shell with an outer edge section with a connection region that does not comprise a core layer along the course of, or along the longitudinal direction of same, or of a section of it. The arrangement, provided according to the invention, of reinforcement devices is thus implemented in such a manner that the reinforcement devices are arranged along an elongated region to be reinforced, or reinforcement region, of the skin field and in the longitudinal direction of the same, one behind the other, in order to, with this measure, prevent transferring shear stress in the skin field. The reinforcement region, or the longitudinal direction of the reinforcement region can be straight or curved.

Generally speaking, i.e. in the various aspects of the invention and/or exemplary embodiments and variants of the invention, for influencing shear stress, the skin shell thus comprises in the core layer a multitude of reinforcement devices, arranged in an intermediate region of the skin shell, which intermediate region extends along the two-dimensional extension of the skin shell. In this regard, it can generally be provided that the reinforcement devices in each case are formed of a combination of at least two reinforcement parts which are disposed in a contiguous spatial part within the skin shell, wherein the reinforcement components are arranged, in the longitudinal direction of the intermediate region or the area to be reinforced, one behind the other, and wherein, with the combination of the reinforcement parts, within a deviation of a maximum of 10 degrees the reinforcement devices in each case have the same orientation relative to the thickness direction of the skin shell, and the alignment of the reinforcement components relative to the further coordinate directions of the skin shell is cyclically provided. In this regard, the alignment of the reinforcement components is generally provided in such a manner that the angle between the longitudinal direction of the respective reinforcement component and the thickness direction of the skin shell at this position is within a range of between 70 degrees and 0 degrees. For the application cases according to the invention it is, in particular, provided that the longitudinal alignment of the reinforcement components is within an angular range of between 45 degrees and 10 degrees. The further coordinate directions are the two coordinate directions that extend in the planar longitudinal extension of the skin shell, in other words the longitudinal direction of the skin shell and the transverse direction of the skin shell. In this arrangement, in addition, at least one further reinforcement component can also be arranged in the volume component, which further reinforcement component is aligned so as to be parallel to a further reinforcement component in the volume component. As an alternative or in addition, generally speaking, further reinforcement components can also be arranged in the volume element. The reinforcement components can in particular be disposed, in a longitudinal direction of the rib arrangement, one behind the other, each comprising pairs of reinforcement components, of each pair of reinforcement components, when viewed in the direction of the longitudinal extension of the skin shell, are oriented to each other in such a manner that the reinforcement components form a reinforcement device that is X-shaped. The reinforcement components can particularly be designed so as to be at least in part pin-shaped.

Furthermore, generally speaking, in the subsequent volume components a variable number and shape of pin-shaped reinforcement components, arranged in the respective contiguous volume components of the skin shell, can be provided, for example in a first volume component two reinforcement components, in the subsequent second volume component four reinforcement components and in the subsequent third volume component three reinforcement components. The volume components are fictitious regions whose borders are defined in such a manner that in said regions the respective arrangement of reinforcement components is arranged or contained. The volume components can, in particular, be defined so as to be in the shape of a rectangular parallelepiped or in the shape of a cube. Various volume components of a sequence of volume components that in the respective longitudinal direction are situated one behind the other can have various sizes of volume components. The volume components can also overlap, when viewed in the longitudinal direction, when a reinforcement component of a volume component engages the interior of a respective adjacent other volume component. The alignment of the volume components is, in particular, provided in such a manner that a centre axis or symmetry axis of the volume components has the same orientation as the orientation of the longitudinal axis of the skin shell, which longitudinal axis is in each case relevant for the arrangement of the reinforcement components. In other words, in the case of a straight longitudinal direction relevant for the arrangement of the reinforcement components the volume components are, in particular, arranged with the same alignment, i.e. said volume components comprise centre axes or symmetry axes that are parallel to each other when the respective relevant longitudinal axis of the skin shell extends in a straight line.

According to the invention, the term "thickness direction of the skin shell" refers to the direction of the shortest separating line between the inner skin section and the outer skin section at the respective position of the skin shell.

The notion of "cyclical arrangement in terms of the further coordinate directions of the skin shell" of the reinforcement components in this context denotes that the alignments of the reinforcement components in terms of the further coordinate directions of the skin shell are cyclically provided. When viewed spatially, this also means that the reinforcement components with the predetermined orientation are distributed regularly or irregularly along a cylinder jacket that extends around the thickness coordinate of the skin shell, which thickness coordinate extends, for example, through the geometric centre of the volume component. In the case of only two reinforcement components the above-mentioned X-shaped arrangement of said reinforcement components results.

According to the invention, the term "longitudinal extension of the skin shell" refers to the local orientation of the centre plane of the skin shell, which, locally or over the entire section of said skim shell under consideration in each case can be curved or non-curved.

The notion of "orientation of the reinforcement components" denotes the direction of the longitudinal axis of the reinforcement components. The longitudinal axis of the reinforcement components can be the symmetry axis, and in the case of an asymmetric and for example curved design of the reinforcement components, orientation of the reinforcement components through the chord of the frontmost point and the rearmost point in the longitudinal direction. The longitudinal direction results from the longest length of the reinforcement components.

According to the invention, the notion of "longitudinal axis of the skin shell relevant for the arrangement of the reinforcement devices" refers to the longitudinal direction of the respective intermediate region.

According to one exemplary embodiment for the design and arrangement of reinforcement devices it can be provided that in at least one volume component or in all the volume components along a longitudinal axis of the skin shell, which longitudinal axis in each case is relevant for the arrangement of the reinforcement components, in each case a pair of reinforcement components or precisely two reinforcement components is/are arranged that are oriented to each other in such a manner that said reinforcement components in each case are arranged in an X-shaped manner when viewed in the longitudinal axis of the skin shell, which longitudinal axis is in each case relevant for the arrangement of the reinforcement components.

According to the invention, the notion of "longitudinal extension of the skin shell" refers to a direction or to a two-dimensional area that is situated in the plane defined by the transverse direction of the skin shell and the longitudinal direction of the skin shell at the respective position.

The reinforcement components can, in particular, be of a pin-shaped or bar-shaped design.

Furthermore, reinforcement components can be of a plate-shaped design. In this arrangement it can, in particular, be provided that in each case at least two plate-shaped reinforcement components, which are X-shaped when viewed in the longitudinal direction of the intermediate region, are arranged so as to engage each other. Furthermore, in this arrangement it can, in particular, be provided that the plate-shaped reinforcement components extend in their width direction, in particular in the longitudinal direct ion of the intermediate region or in the longitudinal axis of the skin shell, which longitudinal axis in each case is relevant for the arrangement of the reinforcement components.

BRIEF DESCRIPTION OF THE DRAWINGS

Below, exemplary embodiments of the invention are described with reference to the enclosed figures, which show the following.

DETAILED DESCRIPTION

The skin shell B or skin plate provided according to the invention is provided as a main-bearing or main-load bearing cladding component or skin component of a flow body and, in particular, of an aerodynamic body. FIG. 1 shows a diagrammatic top view of a structural component 1 or a section of a vertical stabiliser as an example of the flow body according to the invention or of the aerodynamic body. The structural component 1 comprises a support structure T and a skin shell that encloses and is connected to said support structure T. According to the invention, the skin shell B is designed as a sandwich comprising an inner skin section 11, an outer skin section 12 and a thrust-load-absorbing core layer 13 that is situated between the aforesaid, or a thrust-load-absorbing foam core that is situated between the aforesaid. The inner skin section 11 and the outer skin section 12 can in each case comprise fibreglass or a carbon-based material, and can, in particular, be a fibre composite plastic. The inner skin section 11 and the outer skin section 12 in each case extend over the skin shell B. The notion of "inner skin section 11" in terms of its position and orientation refers to a skin section that is situated on the inside of the skin shell B, thus facing an interior or interior space of a structural component 1 or of a flow body that is to be covered by the skin shell B. In the use of the structural component 1 for a flow body the "outer skin section 12" faces the flow which during the intended use occurs on the flow body.

Figure 1A:
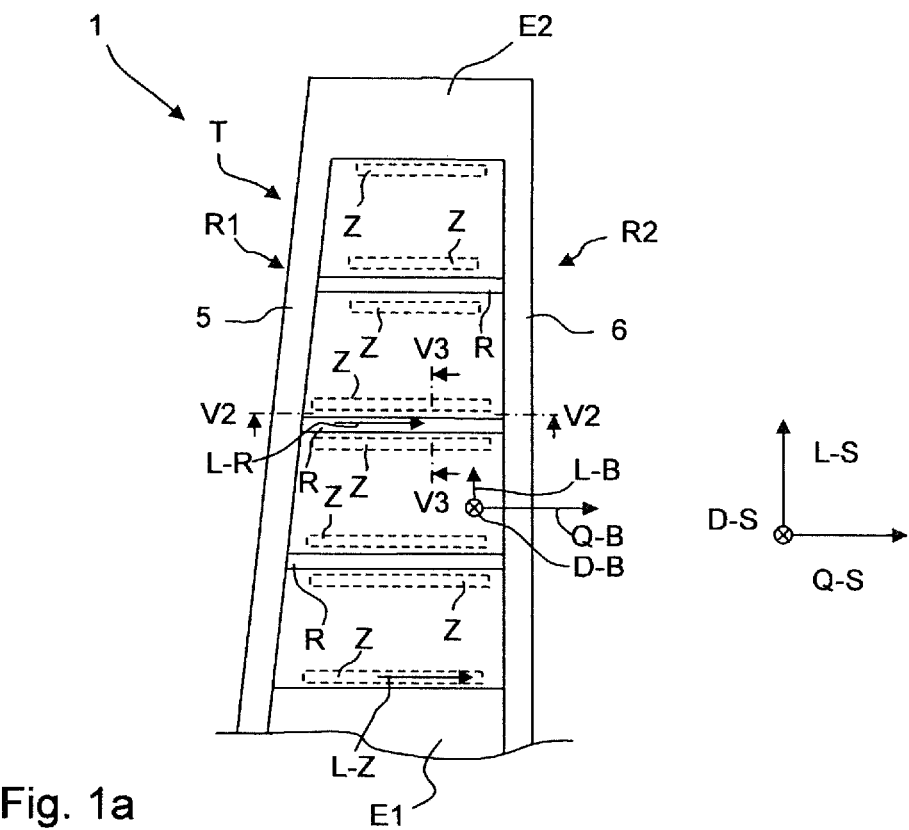
FIG. 1a a diagrammatic top view of a structural component or a section of a vertical stabiliser as an example of the flow body according to the invention with support components and ribs extending between said support components, in which flow body, however, the skin shell provided for the intended use is not shown, wherein diagrammatically the position of intermediate regions or reinforcement regions for the arrangement of reinforcement devices provided according to the invention have been entered, FIG. 1b a section view of the flow body according to FIG. 1a along the line V2-V2 entered in FIG. 1a with the viewing direction also entered in FIG. 1a in the form of two arrows, FIG. 2 a diagrammatic section view of a fictitious volume component as part of the intermediate region of the skin shell with an embodiment of a reinforcement device with reinforcement components that are cyclically arranged in the volume component, FIG. 3a a section view of a region S3 of the flow body of FIGS. 1a and 1b, which is formed along the line V3-V3 entered in FIGS. 1a and 1b with the associated viewing direction in the form of two arrows, which diagrammatic section view relates to a combination, according to the invention, of a support structure with a T-shaped rib arrangement and a skin shell that according to one exemplary embodiment of the invention comprises an inner skin section, an outer skin section and a thrust-load-absorbing core layer arranged between them, FIG. 3b a view of a first embodiment of a cross-sectional shape of reinforcement profiles used in the structural component according to FIG. 3, FIG. 3c a view of a second embodiment of a cross-sectional shape of reinforcement profiles used in the structural component according to FIG. 3, FIG. 4a a section view of the region S3 of the flow body of FIGS. 1a and 1b, which is formed along the line V3-V3 entered in FIGS. 1a and 1b with the associated viewing direction in the form of two arrows, which diagrammatic section view relates to a combination, according to the invention, of a support structure with a T-shaped rib arrangement and a skin shell with an inner skin section, an outer skin section and a thrust-load-absorbing core layer, situated between the aforesaid, in which the attachment of the supporting structure to the skin shell is implemented according to a further exemplary embodiment of the invention, FIG. 4b a section view of the region S3 of the flow body of FIGS. 1a and 1b, which is formed along the line V3-V3 entered in FIGS. 1a and 1b with the associated viewing direction in the form of two arrows, which diagrammatic section view relates to a combination, according to the invention, of a support structure with a T-shaped rib arrangement and a skin shell that comprises an inner skin section, an outer skin section and a thrust-load-absorbing core layer arranged between them, in which skin shell the attachment of the supporting structure to the skin shell is implemented according to a further exemplary embodiment of the invention, FIG. 4c a view of an embodiment according to the invention of a fastener of a fastening device for connecting a connection component of a support structure to the skin shell by means of a fastener, FIG. 5a a cross-sectional view of an exemplary embodiment of a connection region of the skin shell section of the skin shell, which connection region is situated above the rib arrangement, with a reinforcement profile component, wherein in the skin shell between two reinforcement profile components an arrangement of reinforcement devices according to the invention, which reinforcement devices are arranged in an X-shaped manner relative to each other, are integrated, FIG. 5b a cross-sectional view of a further exemplary embodiment of a connection region of the skin shell section of the skin shell, which connection region is situated above the rib arrangement, with a multitude of reinforcement profile components, wherein in the skin shell laterally of the reinforcement profile components an arrangement of reinforcement devices according to the invention, which reinforcement devices are arranged in an X-shaped manner relative to each other, are integrated, FIG. 5c a cross-sectional view of a further exemplary embodiment of a connection region of the skin shell section of the skin shell, which connection region is situated above the rib arrangement, in which skin shell a multitude of reinforcement devices according to the invention, which reinforcement devices are arranged in an X-shaped manner relative to each other, are integrated, FIG. 6a a perspective top view of a first embodiment of a skin shell according to the invention with diagrammatically shown support structures, wherein in the illustration of the skin shell, reinforcement regions or connection regions within the thrust-load-absorbing core layer of the skin shell have been entered diagrammatically, FIG. 6b a perspective top view of a second embodiment of a skin shell according to the invention with diagrammatically shown support structures according to FIG. 6a, in which embodiment the reinforcement regions or connection regions within the thrust-load-absorbing core layer of the skin shell are different from those in FIG. 6a, FIG. 7 a cross section of a first exemplary embodiment of a region, in FIG. 6 designated "A", of the skin shell according to FIG. 7, which region comprises a connection region of a resin, and an embodiment of an arrangement, provided in the context of the connection region, of rib arrangement reinforcement-profiles, FIG. 8 a cross section of a second exemplary embodiment of a region, in FIGS. 6a and 6b designated "A", of the skin shell according to FIG. 6a or 6b, which region comprises a connection region of a resin, and a further embodiment of an arrangement, provided in the context of the connection region, of rib arrangement reinforcement-profiles, FIG. 9 a section of a cross section of the skin shell in which a row of reinforcement devices has been incorporated, each comprising an arrangement of two reinforcement components, which are arranged in an X-shaped manner relative to each other, wherein in FIG. 9 the reinforcement components of a reinforcement device are shown, FIG. 10a a section of a cross section of the skin shell in which two rows, which extend one beside the other, of reinforcement devices have been incorporated, each comprising an arrangement of two reinforcement components, which are arranged in an X-shaped manner relative to each other, wherein in FIG. 10a the two reinforcement components of a reinforcement device are shown, FIG. 10b a section of a cross section of the skin shell in which two rows, which extend one beside the other, of reinforcement devices have been incorporated, each comprising an arrangement of two reinforcement components, which are arranged in an X-shaped manner relative to each other, wherein in FIG. 10a the two reinforcement components of a reinforcement device are shown, wherein the reinforcement devices are arranged in such a manner that the reinforcement components of the various reinforcement devices, when viewed in the longitudinal direction of their extension, mesh or interlock and are arranged relative to each other in the manner of a zipper, FIG. 11 a cross section of an area of the skin shell with a shear-force-absorbing connection region that does not comprise a core layer, the connection region comprising an inner skin section, an outer skin section and a monolithic intermediate layer, wherein at the connection area an area of the skin shell extends in which rib arrangement reinforcement profiles are inserted in the shear-force-absorbing core layer, and FIG. 12 a top view of a section of the skin shell region according to FIGS. 11 to 11.
Figure 1B:
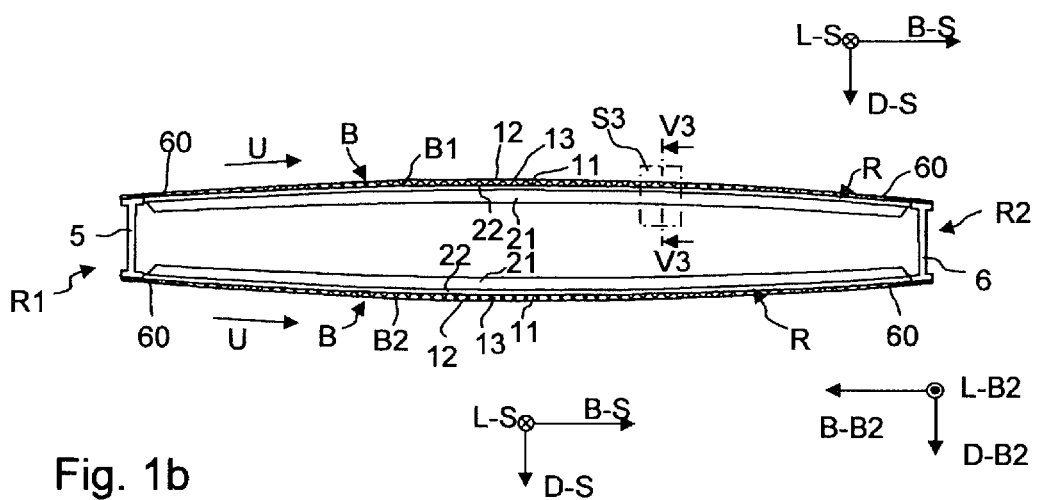

FIG. 1b shows a section along the line V2-V2 entered in FIG. 1a and shows part of a flow body 1 that comprises two skin shells B that are spaced apart from each other, of which a first skin shell B1 and a second skin shell B2 extend along each other and spaced apart from each other. Their outer surfaces form the flow surfaces of the flow body 1. The flow body 1 can, for example, be part of a vertical stabiliser or rudder or part of a wing or of a control flap. In the design of the flow body 1 as a vertical stabiliser or rudder the outsides of the skin shells B1, B2 are preferably designed so as to be axially symmetrical to each other. In the design of the flow body 1 as a wing or as a control flap the outsides of the skin shells B1, B2 can be designed so as to be axially symmetrical or not symmetrical to each other. In particular, in such a use of the flow body 1 on an aircraft with an assumed flow direction U of a main flow which occurs during intended use, for example the outside of the first skin shell B1 can form the suction side, and the outside of the second skin shell B2 can form the pressure side of the flow body.

Figure 11:
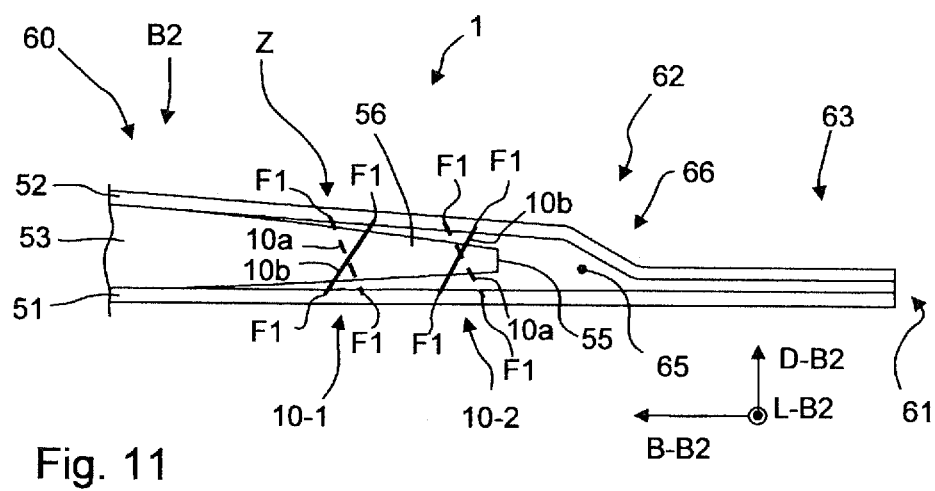
Figure 12:
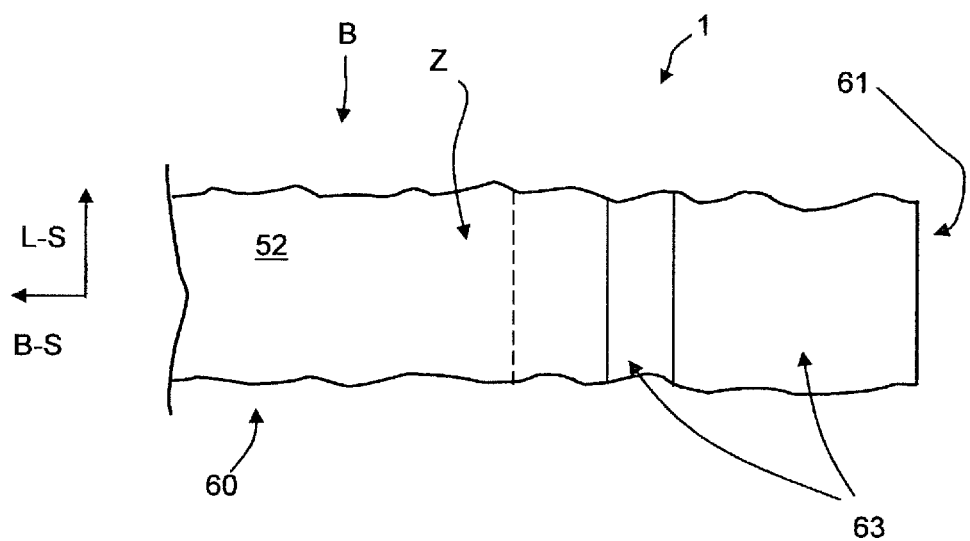

FIG. 1b shows only part of the flow body 1, which when viewed in the width direction or chord direction B-S is delimited by edge sides or edge end pieces R1, R2 formed by the support components 5 or 6 of the support structure T, which support components 5 or 6 extend in the longitudinal direction L-S. On the support components 5, 6 ribs or rib arrangements R have been attached in such a manner that they extend, spaced apart from each other, between the support components 5 and 6. The ribs or rib arrangements R serve as stiffening components for the skin shell components B1 or B2. At their ends situated in the width direction B-S of the structural component 1, the skin shell components B1 or B2 can be designed as edge regions 60 that, for example, in some sections do not comprise a core layer 13 made of foam, which skin shell components B1 or B2 are described with reference to FIGS. 11 and 12. On the skin shell components B1 or B2, when viewed in the width direction B-S of the structural component 1, one behind the other one or several skin shell components B1 or B2 can follow, wherein, in particular, two skin shell components B1 or B2 can be affixed in each case to one 5, 6. As an alternative, a skin shell component B1, B2 on each side or on one of the sides relative to the thickness direction D-S can be held by more than two support components 5, 6. In this arrangement the flow body 1 thus comprises more than two support components 5, 6 that extend so as to be spaced apart from each other in the width direction B-S, and each of the skin shell components B1 or B2 extends between the two support components 5, 6 that in terms of the width direction are the outer support components, and over at least one further support component.

The inner skin section 11 and the outer skin section 12 can in each case be made from fibreglass or from a carbon-based material, and can, in particular, be a fibre composite plastic. The inner skin section 11 and the outer skin section 12 both extend over the skin shell B. The thrust-load-absorbing core layer 13 can, generally speaking, in the invention or in the various aspects of the invention be designed as a solid core or as a foam core. In the embodiment of the core layer as a solid core, the core layer can comprise a plastic, and, in particular, polyethylene and/or polybuthylene. As an alternative or in addition, the core layer can comprise acrylic glass. In the embodiment of the core layer as a foam core, the core layer can comprise a PVC foam or a foamed acrylic glass. According to the invention, for influencing shear stress in the core layer, several reinforcement components and/or reinforcement devices 10 are integrated in the skin shell B, which reinforcement devices 10 in each case project through at least 85% of the thrust-load-absorbing core layer 13 in the latter's thickness direction in order to improve the crack resistance of the skin shell B (not shown in FIG. 1a).

The thrust-load-absorbing core layer 13 can, generally speaking, in the invention or in the various aspects of the invention be designed as a solid core or as a foam core. In the embodiment of the core layer as a solid core, the core layer can comprise a plastic, and, in particular, polyethylene and/or polybuthylene. As an alternative or in addition, the core layer can comprise acrylic glass. In the embodiment of the core layer as a foam core, the core layer can comprise a PVC foam or a foamed acrylic glass.

The support structure T can, in particular, comprise (FIGS. 1a and 3): at least two support components or support profiles 5, 6, each extending one beside the other along a longitudinal direction L-S of the structural component 1 and spaced apart in the chord direction or transverse direction B-S of the structural component 1, and/or at least one rib arrangement R extending between and across said support components, and along their longitudinal direction L-R connected to the skin shell B for two-dimensionally supporting the skin shell B on the support structure T. The width of the stiffening ribs of the rib arrangement R extends in the chord direction T-S of the structural component 1. In the longitudinal direction L-S of the structural component 1 the support components 5, 6 can be connected in each case to an end section E1 or E2. The support components 5, 6 can, in particular, be longitudinal stiffness components or longitudinal members or spars. If, for example, the flow body is an aircraft component, the support components 5, 6 can be longitudinal members or spars of a fuselage, of a wing, of a vertical stabiliser, of a control flap or of a horizontal stabiliser. Each of the rib arrangements R or at least one of several rib arrangements R of the support structure T comprises: a flange component 22 that along the longitudinal direction L-R of the ribs is two-dimensionally connected to the skin shell, and a rib 21 that protrudes from the flange component 22 or from the skin shell B in the transverse direction or chord direction Q-R of said flange component 22. The flange component 22 extends over a length L14 in the width-direction B-R of the rib arrangement R which extends across the longitudinal direction L-R. The rib 21 and the flange component 22 can be produced in one piece. In particular, it can be provided that the rib 21 and the flange component 22 are in each case, separately or together, produced as one component manufactured from fibre composite plastic. In FIGS. 1a and 1b a coordinate system has been entered that relates to the skin shell, with the longitudinal direction L-B of the skin shell, the transverse direction B-B of the skin shell, and the thickness direction D-B of the skin shell as axes.

FIG. 1a also shows intermediate regions or regions of the foam core, which regions are to be reinforced with the reinforcement devices 10 provided according to the invention.

Since the skin shell B has been fastened to the support structure T in order to form an outside of the flow body, and is thus essential in producing a flow around the flow body, said skin shell B is a main-load bearing structural part of the structural component 1.

The main-load bearing skin shell B according to the invention can, in particular, be used for the manufacture of such a structural component 1. Since the skin shell B has been fastened to the support structure T in order to form an outside of the flow body, and is thus essential in producing a flow around the flow body, and in this process takes up the external forces produced by air, and to a predetermined extent is to compensate for the effects of objects impacting the skin shell B, said skin shell B is a main-load bearing structural part of the structural component 1. In the compensation of effects resulting from objects impacting the skin shell B, the skin shell B according to the invention ensures that after the impact of said objects said skin shell B remains as an entity that is stable overall, which entity then continues to take up the forces associated with flow.

Figure 3A:
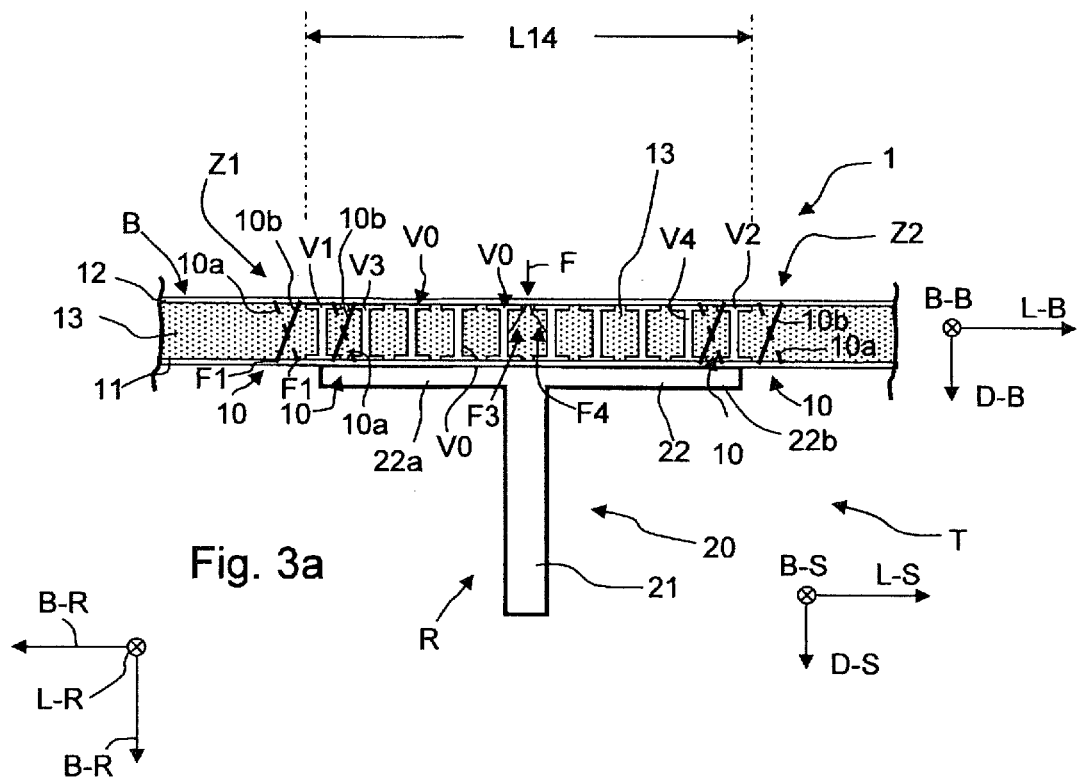

FIG. 3a shows an embodiment of a combination, according to the invention, of a T-shaped rib-arrangement R and a skin shell 22 which according to the invention comprises an inner section 11, an outer skin section 12, and a thrust-load-absorbing core layer 13 situated between the aforesaid. FIG. 3a shows a section view of a region S3 of the flow body 1 of FIGS. 1a and 1b, which is formed along the line V3-V3 entered in FIGS. 1a and 1b with the associated viewing direction in the form of two arrows, which diagrammatic section view relates to a combination, according to the invention, of a support structure with a T-shaped rib arrangement and a skin shell B. According to an exemplary embodiment of the invention, the skin shell B in terms of the flow body 1 comprises an inner skin section 11, an outer skin section 12, and a thrust-load-absorbing core layer 13 arranged between them. According to the invention, in the core layer 13, laterally of the rib arrangement R, reinforcement devices 10 or rib-arrangement reinforcement profile components can have been inserted. Generally speaking, the support structure T can also comprise a support arrangement, only one rib 21 without a plate-shaped connection piece 22, or it can be a support arrangement that comprises only a plate-shaped connection piece 22. According to the invention, in this arrangement it can be provided that in the skin shell B along a skin shell section that extends across the longitudinal direction L-R of the rib arrangement, which skin shell section forms a connection region 14 of the support structure T, in other words, for example, of a support component 5, 6 and/or of the rib arrangement R on the skin shell B, one or several profile carriers or rib arrangement reinforcement-profile components V0 have been inserted or integrated. For example, for the reinforcement of the skin shell B in the connection region of a support component 5, 6 on said skin shell B or in the connection region of a support arrangement or rib arrangement R, profile carriers are arranged as support component reinforcement profile carriers or support component reinforcement profile components or rib-arrangement reinforcement profile carriers or support component reinforcement profile components. The connection region 14 is that region of the skin shell B in whose two-dimensional extension, which when viewed in the thickness direction D-B of the skin shell B, covers or intersects the region that delimits the support structure T or the support component 5, 6 or the support arrangement or rib arrangement R by its side facing the skin shell B, or in whose limits the respective support structure T rests against the skin shell B. In the embodiment shown with the rib arrangement R, the side of the support structure T, which side faces the skin shell B, is the side of the flange component of the rib arrangement R, which side faces the skin shell B. The profile carriers V0 interconnect the flange component 22 or the inner skin section 11 and the outer skin section 12 for stabilising the skin shell B during damage from the outside.

The at least one profile carrier V0 or the profile carriers V0 can be designed as elongated or plate-shaped reinforcement profile carriers. In this arrangement the profile carriers V0 can extend in a reference longitudinal direction that is oriented in the longitudinal extension of the respective support structure T. The longitudinal extension of the support components according to FIG. 1a thus extends along the edge region of the skin shell B, which edge region rests against the adjacent edge region of the skin shell B so that in this respect the reference longitudinal direction of the profile carriers V0 extends along the edge region of the skin shell B. The reference longitudinal direction of a support arrangement or of a rib arrangement R extends in the direction of the longitudinal extension of the aforesaid and, in particular, along the support arrangement direction or longitudinal direction L-R of the rib arrangement, i.e. parallel to the support arrangement direction or longitudinal direction L-R of the rib arrangement or obliquely to it. If several profile carriers V0 are provided, they can, in particular, when viewed in a reference longitudinal direction that in the exemplary embodiment shown is the longitudinal direction L-R of the rib arrangement, be arranged one beside the other and extend one beside the other.

In this arrangement the reference longitudinal direction is the direction of extension of a region that is to be reinforced by means of the profile carriers V0 or that is to be stabilised for load cases. In particular, the region that is to be reinforced or stabilised can be the connection region of a support structure T, for example of a support component 5, 6 or a rib arrangement R. This can, in particular, be the connection region of the flange component 22 and of the skin shell B. By providing the profile carriers V0, crack formation in the core layer 13 due to major stress in the core layer 13, which stress results from external loads acting on this region, is prevented and/or locally stopped. Calculations and extensive trials have demonstrated the positive effect of these solution measures according to the invention.

In this context the term "longitudinal direction L-R of the rib arrangement" refers to the direction that extends along the longitudinal extension of the skin shell B and along the longitudinal direction of the rib 21. If several ribs are provided, the longitudinal direction L-R of the rib arrangement can, in particular, extend along the longitudinal direction of one of these ribs or of a main rib. The term "transverse direction Q-R of the rib arrangement" refers to the direction that extends perpendicularly to the longitudinal direction L-R of the rib arrangement and across the longitudinal extension of the skin shell B and in the width direction, in other words the main extension of the rib 21. FIG. 3 also shows the rib-arrangement width direction B-R, which is oriented perpendicularly to the longitudinal direction L-R of the rib arrangement and to the transverse direction Q-R of the rib arrangement.

In this embodiment of the invention with a support structure T attached to a skin plate the connection component 22 for attachment of it to the skin shell can be two-dimensionally bonded to the inner skin section. In addition or as an alternative to this, the connection component with the skin shell can be connected to the inner skin section by means of fasteners such as, in particular, rivets, as shown in FIGS. 4a, 4b, 4c.

In the exemplary embodiment shown in FIG. 3a several rib arrangement reinforcement profile components V0 are arranged one behind the other when viewed in the width direction B-R of the rib, or one beside the other when viewed in the longitudinal direction L-R of the rib arrangement. FIG. 3 shows an embodiment of the rib arrangement R in which rib arrangement reinforcement profile components V0 are distributed over the entire connection region of the flange component 22 and the skin shell B. In the cross section, shown in FIG. 3, of an exemplary embodiment of the rib arrangement R a total of ten rib arrangement reinforcement profile components V0 are situated one beside the other when viewed in the longitudinal direction L-R of the rib arrangement. In FIG. 3 the outer reinforcement profile carriers V0, when viewed in the longitudinal direction L-R of the rib arrangement, are designated by the reference characters V1, V3 or V2, V4. Generally speaking, the rib arrangement profile components V0, can, in particular, be distributed so as to be evenly spaced apart in the entire region of the flange component 22 or over a section of the flange component 22.

Figure 3B:
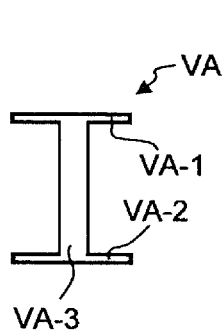

In an embodiment of the reinforcement profile carrier V0 shown in FIG. 3b, said reinforcement profile carrier (reference character VA) can comprise two profile plates VA-1, VA-2, one of which is connected to the inner skin section 11, and the respective other one is connected to the outer skin section 12, and a support rib VA-3 that connects the aforesaid so that its profile cross section is a double-T profile cross section.

Figure 3C:
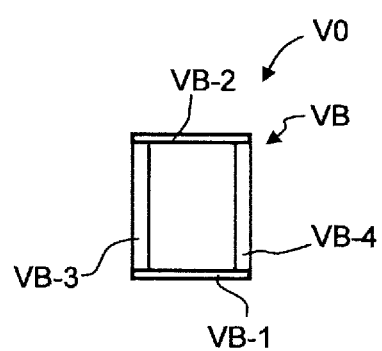

In an embodiment, shown in FIG. 3c, of the reinforcement profile carrier V0 the latter (reference character VB) can be designed in such a manner that the profile cross section of the reinforcement profile carrier is a box-shaped profile cross section. In this arrangement the reinforcement profile carrier VB can comprise two profile plates VB-1, VB-2, one of which is connected to the inner skin section 11, and the respective other one is connected to the outer skin section 12, and two support ribs VB-3, VB-4 that connect the aforesaid so as to form a box-profile cross section.

FIG. 4a shows a section view of the region S3 of the flow body of FIGS. 1a and 1b, which is formed along the line V3-V3 entered in FIGS. 1a and 1b with the associated viewing direction in the form of two arrows, which diagrammatic section view relates to a combination, according to the invention, of a support structure with a T-shaped rib arrangement and a skin shell B, with an inner and an outer skin section 11,12 and a thrust-load-absorbing core layer 13 situated between the aforesaid, in which arrangement the connection component 22 with the skin shell B is attached to the inner skin section 12 by means of fasteners 16. As an example, the position of the fasteners 16 is shown by means of the position lines 15a and 15b. In particular, it can be provided that viewed in the plane defined by the longitudinal direction L-B and the thickness direction D-B, laterally of the rib 21, fasteners 16 interconnect the connection component 22 and the outer skin section 12, which fasteners 16 can, in particular, in each case form at least one row of fasteners 16 that extends in the width direction B-B. The rows can, in particular, also extend parallel to each other. The rows can also be formed by fasteners 16 that are regularly spaced apart from each other.

As shown with reference to the embodiment according to FIG. 4, in particular, in the area of the connection region 14 no profile carriers of the type according to the embodiment according to FIG. 3a need to be arranged between the skin sections 11, 12. The arrangement of fasteners 16 for connecting the connection component 22 to the outer skin section 12 can be provided as set out with reference to the exemplary embodiment according to FIG. 4a.

As an example of the fastener 16 that can be used according to the invention, FIG. 4c shows a rivet that fastens the connection component 22 to the skin section 12.

In the connection region it can, in particular, be provided that the inner skin section, against which the connection component 22 rests, comprises a greater material thickness than the inner skin section laterally of the connection region. According to one embodiment of the invention, this thickening in terms of its two-dimensional extent can be in a region that deviates by a maximum of ten times the thickness of the skin shell from the edge contour of the connection region. This increase in thickness can be implemented by arranging further layers in this two-dimensionally extending region on the core layer and/or on the surface of the inner skin section, which surface faces the outside of the skin shell.

In the embodiment of the combination of the skin shell B and of a support component 5, 6 and/or of the rib arrangement R on the skin shell B according to FIG. 4a, in the connection region 14 of the skin shell B and optionally in the width direction B-R laterally beside the connection region 14, reinforcement components 10a, 10b, or reinforcement devices 10, in particular, according to a type provided according to the invention and/or a type described in this document are arranged. In this arrangement, reinforcement components 10a, 10b or reinforcement devices 10 can be arranged in a row when viewed in the width direction B-R of the rib arrangement, or one beside the other in the width direction of the support component, and/or in the longitudinal direction L-R of the rib arrangement or in the longitudinal direction of the support component. In these cases, as shown in FIG. 4a, pairs of reinforcement components 10a, 10b can also in each case in an X-shaped arrangement have been incorporated in the skin shell B. Generally speaking, the reinforcement components extend in the thickness direction of the skin shell B or obliquely to the aforesaid, and in this arrangement can be situated within the core layer 13 in such a manner that their ends F1 are spaced apart from the skin sections 11, 12, or one of their ends F1 is spaced apart from one of the skin sections 11, 12, or the reinforcement components can be situated in such a manner that in each case they interconnect the inner and the outer skin sections 11, 12, in other words partly penetrate the inner and/or outer skin section 11, 12. The inner skin section 51 and/or the outer skin section 52 can in each case comprise several skin layers, and/or at least part of the reinforcement devices 10, 10a, 10b, 10c, 10d; 10e, 10f can be arranged in such a manner that their ends F1 or one of their ends F1 project/s through the inner skin section 51 and/or through the outer skin section 52, in each case at least the first skin layer. Generally speaking, the reinforcement components thus at least in part project through the thrust-load-absorbing core layer 13.

By means of the arrangement of the reinforcement device 10 along the rib arrangement R it becomes possible that damage to the skin shell B, for example in the form of cracks in the thrust-load-absorbing core layer 13, in the region of the rib arrangement R does not transfer or transfers to a reduced extent to the two-dimensionally extending region of the skin shell B, which region extends beside the rib arrangement R. Furthermore, conversely, by arranging the reinforcement device 10 along the rib arrangement R it becomes possible that damage to the skin shell B, for example in the form of cracks in the thrust-load-absorbing core layer 13 in the two-dimensionally extending region of the skin shell B, which region extends beside the rib arrangement R, does not transfer or transfers to a reduced extent to the region of the skin shell B, which region is situated in the region of the rib arrangement R.

According to one exemplary embodiment of the structural component 1 according to the invention, between rib arrangement reinforcement profile components V0 of the rib arrangement R that are situated one beside the other when viewed in the longitudinal direction L-R of the rib arrangement at least one reinforcement device 10 is arranged. According to the exemplary embodiment shown in FIG. 3a, between the outer rib arrangement reinforcement profile components V1 and V3 or V2 and V4, when viewed in the transverse direction Q-R of the rib arrangement, reinforcement devices 10 according to the invention are arranged. This constellation can be provided several times one behind the other in the longitudinal direction L-R of the rib arrangement. Furthermore, in each case between several rib arrangement reinforcement components, in other words for example between two, three or four outer rib arrangement reinforcement components, in each case at least one reinforcement device 10 according to the invention can be arranged. In this arrangement the reinforcement device 10 and the respectively associated rib arrangement reinforcement components can also be arranged so as to be offset relative to each other, when viewed in the transverse direction Q-R of the rib arrangement. In these exemplary embodiments these constellations preferably occur repeatedly, situated one behind the other in the longitudinal direction L-R of the rib arrangement, and can be distributed over the length of the rib arrangement R in the skin shell B.

In the combination according to the invention of a skin shell B and of a rib arrangement R it is also possible for reinforcement components and/or at least one reinforcement device 10 to be arranged in the skin shell instead of rib arrangement reinforcement profile components V0 according to one of the types described herein.

FIG. 3a diagrammatically shows a crack formation in the foam core 13: an object F1 impacts with a pulse F the skin shell B. The resulting cracks in the foam core 13 are shown by reference characters F3 and F4.

In the embodiments of the skin shell B provided according to the invention the reinforcement devices 10 can, generally speaking, in each case comprise at least one reinforcement component. In this arrangement a reinforcement component can be designed as a stud-shaped reinforcement component comprising, for example, a round or rectangular cross-sectional shape.

The reinforcement devices 10 in each case comprise at least one reinforcement component 10a, 10b, 10c, 10d, 10e, 10f. Such a reinforcement component 10a, 10b, 10c, 10d, 10e, 10f can, in particular, be designed as an elongated and/or plate-shaped element. The reinforcement components 10a, 10b, 10c, 10d, 10e, 10f can thus, in particular, be pin-shaped. In FIGS. 2, 5a, 5b, 9, 10a, 10b the respectively shown reinforcement components 10a, 10b, 10c, 10d, 10e, 10f comprise the reference characters 10a, 10b, 10e or 10f.

Figure 5A:
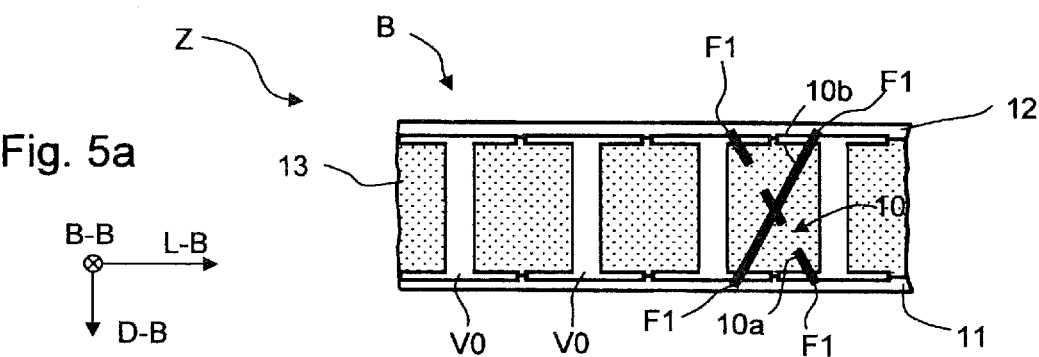
Figure 5B:
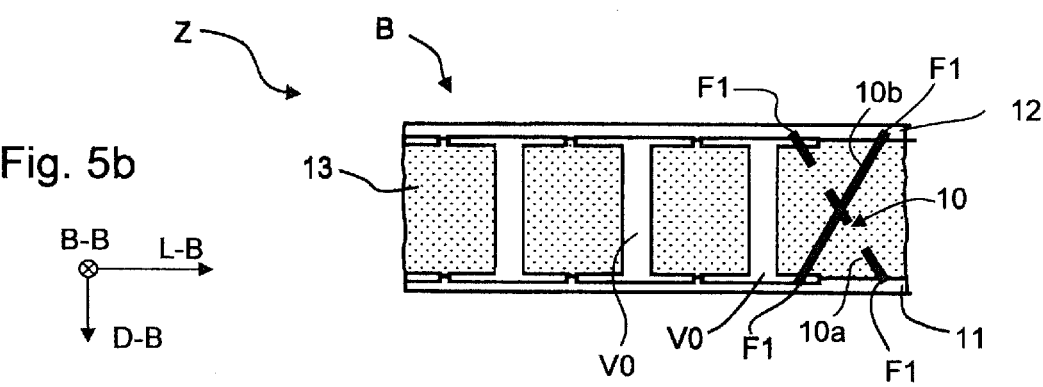
Figure 5C:
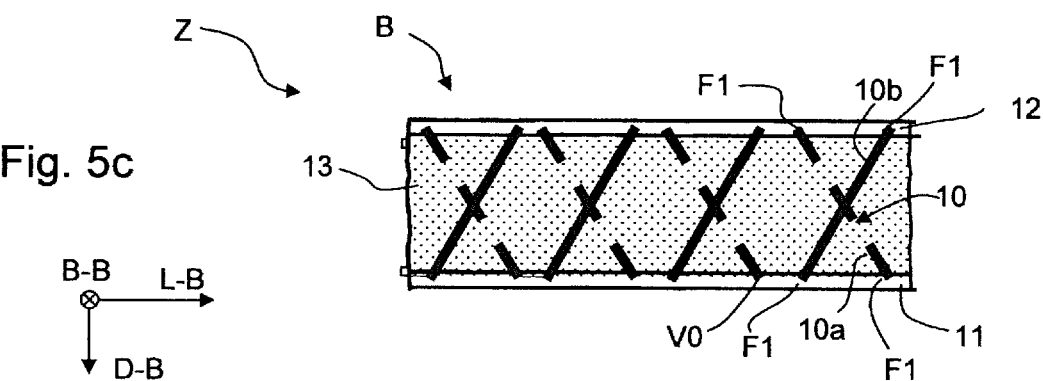

According to a further embodiment, shown in FIG. 5c, according to the invention, of the combination of the skin shell B and of a support component 5, 6 and/or of the rib arrangement R on the skin shell B it can be provided that in the connection region 14 of the skin shell B and optionally in the width direction B laterally beside the connection region 14, reinforcement components 10a, 10b, 10c, 10d, 10e, 10f or reinforcement devices 10, in particular, according to a type provided according to the invention and/or a type described in this document are arranged. In this arrangement it is, in particular, provided that no profile components have been inserted in the connection region 14 (FIG. 5c). In this arrangement, reinforcement components 10a, 10b, 10c, 10d, 10e, 10f or reinforcement devices 10 can be arranged in a row in the width direction B-R of the rib arrangement or in the width direction of the support component one beside the other and/or in the longitudinal direction L-R of the rib arrangement or in the longitudinal direction of the support component. In these cases, as illustrated in FIG. 5c, it is also possible for pairs of reinforcement components 10a, 10b, 10c, 10d, 10e, 10f in each case in an X-shaped arrangement to have been incorporated in the skin shell B.

Generally speaking, the reinforcement components extend in the thickness direction of the skin shell B or obliquely to the aforesaid, and in this arrangement can be situated within the core layer 13 in such a manner that their ends F1 are spaced apart from the skin sections 11, 12, or one of their ends F1 is spaced apart from one of the skin sections 11, 12, or the reinforcement components can be situated in such a manner that in each case they interconnect the inner and the outer skin sections 11, 12, in other words partly penetrate the inner and/or outer skin sections/section 11, 12. The inner skin section 51 and/or the outer skin section 52 can in each case comprise several skin layers, and/or at least part of the reinforcement devices 10, 10a, 10b, 10c, 10d; 10e, 10f can be arranged in such a manner that their ends F1 or one of their ends F1 project/s through the inner skin section 51 and/or through the outer skin section 52, in each case at least the first skin layer. Generally speaking, the reinforcement components thus at least in part project through the thrust-load-absorbing core layer 13.

The reinforcement components can, in particular, be situated in the skin shell B in such a manner that the angle between the longitudinal direction of the respective reinforcement component and the thickness direction of the skin shell at this position is within a range of between 45 degrees and 10 degrees.

The reinforcement devices 10 provided according to the invention can, generally speaking, be arranged one behind the other when viewed in a reference longitudinal direction, which in the exemplary embodiment shown is the longitudinal direction L-R of the rib arrangement. Furthermore, reinforcement components V can also be arranged one behind the other when viewed across the reference longitudinal direction or the longitudinal direction L-R of the rib arrangement. In this arrangement reinforcement devices 10 can be arranged in several rows of reinforcement devices 10, which extend one beside the other. Such rows of reinforcement devices 10 can also be arranged so as to mesh or interlock (FIG. 10b) in which the reinforcement devices 10 overlap in the reference longitudinal direction or longitudinal direction L-R of the rib arrangement, wherein the reinforcement devices 10 can also be situated so as to be spaced apart from each other in the reference longitudinal direction or longitudinal direction L-R of the rib arrangement. In particular, several rows of reinforcement components can extend one beside the other.

The reference direction in terms of the arrangement of reinforcement devices 10 or reinforcement components is the direction of extension of a region that by means of a multitude of reinforcement devices 10 or reinforcement components is to be reinforced or stabilised for load cases. Hereinafter this region is also referred to as the reinforcement region or intermediate region Z. In particular, the region that is to be reinforced or stabilised can for example extend laterally or within and/or along a connection region of a support component, for example of a rib arrangement, or along an edge region and thus can be a transition region from the connection region or the edge region to the two-dimensional region of extension of the skin shell B, in which region crack formation in the core layer 13 due to major stress resulting in this region in the core layer 13 can be prevented or locally stopped. Calculations and extensive trials have demonstrated the positive effect also of these solution measures according to the invention.

In the exemplary embodiment, shown in FIG. 3*a*, of affixing the skin shell B to a rib arrangement R, and of reinforcement components, shown in FIGS. 5*a*, 5*b*, 9, 10*a*, 10*b*, the aforesaid are in each case diagrammatically shown as dot-dash lines, wherein, in the section shown, a solid line designates reinforcement components that are situated in the cut surface, while a dot-dash line designates reinforcement components arranged in a sectional plane that is spaced apart from this sectional plane.

Generally speaking, the reinforcement components or the reinforcement devices can be arranged along the above-mentioned reference longitudinal direction one behind the other and in a row or in several rows one beside the other. In the exemplary embodiment shown in FIG. 3, reinforcement components along the above-mentioned reference longitudinal direction and for example the longitudinal direction L-R of the rib arrangement are arranged one behind the other. In this arrangement the pin-shaped elements can be arranged so as to be offset relative to each other, when viewed in a straight line one behind the other or in the longitudinal direction L-R of the rib arrangement, i.e. they can also be spaced apart from each other across the longitudinal extension of the skin shell B.

In this exemplary embodiment of FIG. 3*a* it is, furthermore, provided that reinforcement components 10*a*, 10*b* are arranged within two lateral regions Z1, Z2 of the skin shell B, which reinforcement components 10*a*, 10*b* extend in longitudinal direction L-R of the rib arrangement and laterally along the lateral ends of the skin shell section 14, with the width of said reinforcement components 10*a*, 10*b* in each case extending across the longitudinal direction L-R of the rib arrangement, and in the longitudinal extension of the skin shell B.

As an alternative or in addition, it can be provided that reinforcement components 10*a*, 10*b* have been inserted in a reinforcement region, which reinforcement components 10*a*, 10*b* are situated within the skin shell section 14 and laterally along the lateral ends of the skin shell section 14 in the core layer 13. In FIG. 3*a* such groups of reinforcement components are designated by reference characters V3 and V4.

Generally speaking, the embodiments of the skin shell B according to the invention, for influencing shear stress and to avoid crack formation in the core layer 13, can comprise a multitude of reinforcement components which are disposed in at least one reinforcement area or intermediate Z of the skin shell B or reinforcement devices 10 which are defined according to the invention, that are arranged at least in one reinforcement region or intermediate region Z of the skin shell B, which reinforcement devices 10 in each case comprise a combination of at least two reinforcement components arranged in a contiguous volume component V (FIG. 2) of the skin shell B. The at least one intermediate region Z of the skin shell B has been selected in such a manner in size and position that said intermediate region Z stabilises the entire skin shell B based on the external loads expected in a given case of application, in that the shear stress arising in the respective intermediate region Z as a result of these loads, because of the presence of the reinforcement components does not result in crack formation in the core layer 13 of this intermediate region Z, or stops crack formation. In this arrangement the position and size of the at least one intermediate region Z and the type of arrangement of the reinforcement components therein are preferably selected in such a manner that not only within but also outside the intermediate region Z the danger of crack formation in the core layer 13 of the skin shell B is minimised. In this arrangement the position and size of the at least one intermediate region Z depend on the application case, in other words the design of the entire structural component with the skin shell B, with the associated assumed external loads.

According to one embodiment of the invention, the reinforcement components of the reinforcement devices 10 can be arranged in groups. In this arrangement it can, in particular, be provided that the reinforcement components 10*a*, 10*b*, 10*c*, 10*d* or 10*e*, 10*f* of a reinforcement device 10 are arranged in groups in each case in one of several volume components V of the skin shell B (FIG. 2), wherein generally speaking each group of reinforcement components 10*a*, 10*b*, 10*c*, 10*d* or 10*e*, 10*f* in each case comprises a fictitious volume component V, in each case comprising a combination of at least two reinforcement components 10*a*, 10*b*, 10*c*, 10*d* or 10*e*, 10*f*. Thus in each case in a contiguous volume component V of the skin shell B a group of reinforcement components is arranged. The reinforcement components 10*a*, 10*b*, 10*c*, 10*d* or 10*e*, 10*f* of a group of the aforesaid in each case have a similar position or orientation within the skin shell B, and in each case with a deviation of a maximum of 30 degrees have the same orientation relative to the thickness direction D-B of the skin shell B. In particular, it can, furthermore, be provided that the alignments of the reinforcement components of a group relative to the further coordinate directions L-B, B-B of the skin shell B are cyclically provided.

Figure 2:
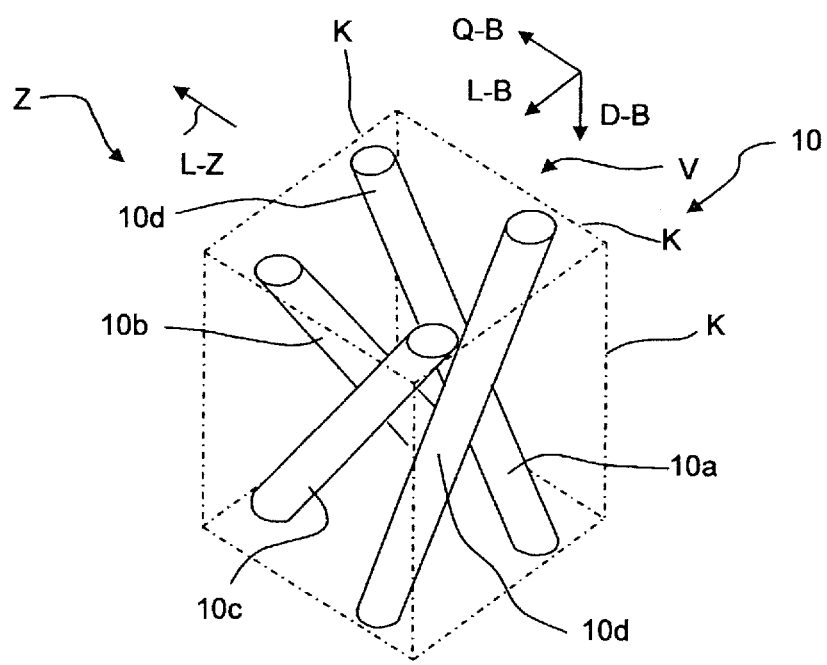

One example of a group of four reinforcement components 10*a*, 10*b*, 10*c*, 10*d* with cyclical orientation among them is shown in FIG. 2. FIG. 2 shows an exemplary embodiment of such a fictitious volume component V in the form of a rectangular parallelepiped with the edge lines K. For guidance, FIG. 2 also shows the longitudinal direction L-Z of the intermediate region Z, and the coordinate system of the skin shell with the coordinate axes L-B, Q-B and D-B of said skin shell. The arrangement of the reinforcement devices 10 is, in particular, provided in the longitudinal direction L-Z of the intermediate region Z one behind the other. In the exemplary embodiment according to FIG. 2 the reinforcement device 10 shown comprises a combination of four reinforcement components 10*a*, 10*b*, 10*c*, 10*d*, wherein in the combination of the reinforcement components 10*a*, 10*b*, 10*c*, 10*d* the aforesaid in each case with a deviation of a maximum of 10 degrees have the same orientation in terms of the thickness direction D-B of the skin shell B, and wherein the alignment of the reinforcement components in terms of the further coordinate directions L-B, B-B of the skin shell B is cyclical.

In this arrangement the reinforcement devices 10 or a multitude of reinforcement devices 10 according to the invention can, generally speaking, be situated on an imaginary line that extends along, i.e. parallel or at an angle to the reference line or to the longitudinal direction L-R of the rib arrangement, and/or also offset relative to each other when viewed across the longitudinal direction L-R of the ribs.

In a special case a group of reinforcement components can comprise two reinforcement components 10*e*, 10*f* which can be arranged in an approximately X-shaped manner relative to each other when viewed in the above-mentioned reference longitudinal direction. In this embodiment of the skin shell B thus at least part of the reinforcement devices 10 comprise reinforcement components 10*a*, 10*b*, 10*c*, 10*d*; 10*e*, 10*f* whose reinforcement components in pairs comprise X-shaped orientations when viewed in the direction of a longitudinal extension of the skin shell B. In such a group of X-shaped reinforcement components the two reinforcement components can be arranged so as to be spaced apart from each other or can rest against each other or can have been inserted as a cross-shaped structure into the skin shell B. For example, several pairs of reinforcement devices 10, each positioned on one of the two sides Z1, Z2, are oriented relative to each other in such a manner that in each case one of these pairs forms an X-shaped reinforcement device when viewed in the longitudinal direction L-R of the rib arrangement.

The reinforcement devices 10 can be designed and constructed in various ways. According to an exemplary embodiment according to the invention it is provided that the reinforcement devices 10 comprise a multitude of combinations of pin-shaped reinforcement components 10e, 10f, which are situated one behind the other when viewed in the longitudinal direction L-R of the rib arrangement, wherein each pair of reinforcement components 10e, 10f is arranged in a volume component V according to the invention. It is also possible for part or all of the reinforcement components inserted in a skin shell B or in a region thereof to be of a pin-shaped design. Furthermore, at one of their ends or on both of their ends the reinforcement components can in each case comprise a foot-like widened part or a hook that can be provided for positioning and/or spatial affixation or anchoring within the skin shell B. This design of reinforcement components can be associated with an advantage in that when an external dynamic damage load is experienced, the respective reinforcement components remain affixed in the skin shell B.

As an alternative to this the reinforcement devices can comprise a multitude of combinations of plate-shaped reinforcement components (not shown in the figures) which in each case in their first longitudinal extension extend between the inner skin section 11 and the outer skin section 12 and through the thrust-load-absorbing core layer 13 that is situated between said skin sections 11 and 12. In their longitudinal direction that is aligned so as to be perpendicular to the first longitudinal extension, these plate-shaped reinforcement components extend in the longitudinal direction L-R of the rib arrangement.

In this arrangement the for example pin-shaped or plate-shaped reinforcement components 10e, 10f, in particular, of respective pairs of the aforesaid can rest against each other. Moreover, pin-shaped or plate-shaped reinforcement components 10e, 10f, in particular of respective pairs of the aforesaid, can be spaced apart from each other in the longitudinal direction L-R of the rib arrangement. According to one exemplary embodiment, in this arrangement it can be provided that the distance between the pin-shaped or plate-shaped reinforcement components 10e, 10f in each case of a pair of the aforesaid comprises a maximum of 1.5-times the thickness of the skin shell B at the respective position.

In the design of the reinforcement devices as plate-shaped reinforcement components, two or several of the latter can also in each case be arranged so as to mesh or interlock when viewed in the longitudinal direction L-R of the rib arrangement.

In the embodiments of the reinforcement devices 10 according to the invention the reinforcement devices 10 or a multitude of the latter can also extend through the inner skin section 11 and the outer skin section 12, or in each case can be anchored in said skin sections 11, 12 by an end section. As an alternative or in addition, reinforcement devices 10 or a multitude of them, by their respective end sections that face the skin sections, can rest against the inner skin section 11 and the outer skin section 12, or can in each case end at a distance from said skin sections 11, 12.

Generally speaking, it can be provided that at least part of the reinforcement devices 10; 10a, 10b, 10c, 10d; 10e, 10f are arranged in the skin shell B in such a manner that in each case their ends F1 at least in part project through the inner skin section 11 and/or the outer skin section 12 as shown in FIGS. 5a, 5b, 7, 8, 9, 10a, 10b and 11.

The inner skin section 11 or 51 (FIG. 11) and/or the outer skin section 12 or 52 (FIG. 11) can in each case comprise several skin layers (not shown in the figures). In this arrangement it can, in particular, be provided that at least part of the reinforcement devices 10a, 10b, 10c, 10d are arranged in the skin shell B in such a manner that in each case their ends F1 at least in part project through the inner skin section 11 or 51 and/or the outer skin section 12 or 52.

According to the invention, the reinforcement components can, generally speaking, comprise a metallic material and/or a non-metallic material and, in particular, a fibre composite plastic material. Carbon, fibreglass, quartz, Kevlar and/or ceramics can be used as non-metallic materials.

According to a further embodiment of the structural component according to the invention, the thrust-load-absorbing core layer 13 comprises at least one core layer reinforcement region 37 and preferably a multitude of core-layer reinforcement regions 37 (FIG. 4), by means of which several thrust-load-absorbing core-layer sections 33a, which in the longitudinal extension of the thrust-load-absorbing core layer 33 or of the foam layer are arranged one beside the other, are connected. Each core layer reinforcement region 37 extends in a longitudinal direction L-V of the core layer (FIG. 3) across the longitudinal extension of the thrust-load-absorbing core layer 13 through the aforesaid and in this process extends between the inner skin section 11 and the outer skin section 12. In FIG. 3 an exemplary embodiment of the structural component according to the invention is shown, wherein the dot-dash lines show the edge lines of the individual thrust-load-absorbing core-layer sections 33a or the course of the core-layer reinforcement regions 37. In the embodiment of the structural component according to FIG. 3 the courses of the core-layer reinforcement regions 37 are provided in such a manner that rectangular thrust-load-absorbing core-layer sections 33a result, or that, conversely, the core layer comprises core-layer sections 33a that are interconnected by way of core-layer reinforcement regions 37. In this arrangement it can, in particular, be provided that the core-layer reinforcement region 37 is connected to the inner skin section 11 and the outer skin section 12 so that the core layer reinforcement region 37 is connected to the inner skin section 11 and the outer skin section 12.

According to one embodiment of the skin shell B, the thickness 17a of the core-layer reinforcement region 37 is between 0.1-times and 2.0-times the width of the skin shell B at this position, wherein the thickness is measured perpendicularly to the longitudinal extension of the skin shell.

By means of reinforcement devices 10 inserted in the core layer reinforcement region 37, transmission of damage to the skin shell B, in particular in the form of cracks in the thrust-load-absorbing core layer from one side of the core-layer reinforcement region 37 to the respective other side of the core-layer reinforcement region 37 can be more effectively prevented or stopped.

The reinforcement region comprises a material that provides at least twice the stiffness of the thrust-load-absorbing core layer 13. In this arrangement the core-layer reinforcement region 37 can, in particular, comprise resin.

In an embodiment, according to the invention, of the skin shell B with a rib arrangement R it can also be provided that several reinforcement components 10, designed according to one embodiment of the invention and situated one behind the other along the longitudinal direction L-R of the rib arrangement, in each case project through the at least one core layer reinforcement region 37. The core-layer reinforcement region 37 can, in particular, in its longitudinal direction extend along the longitudinal direction L-R of the rib arrangement and along a section or along the entire length of the rib arrangement R. In this arrangement the core-layer reinforcement region 37 can extend so as to be parallel or at an angle to the longitudinal direction L-R of the rib arrangement. At least one core layer reinforcement region 37 with reinforcement devices arranged on the aforesaid can, in particular, be provided in at least one of the two lateral regions Z1, Z2 that extend in longitudinal direction L-R of the rib arrangement.

Figure 7:
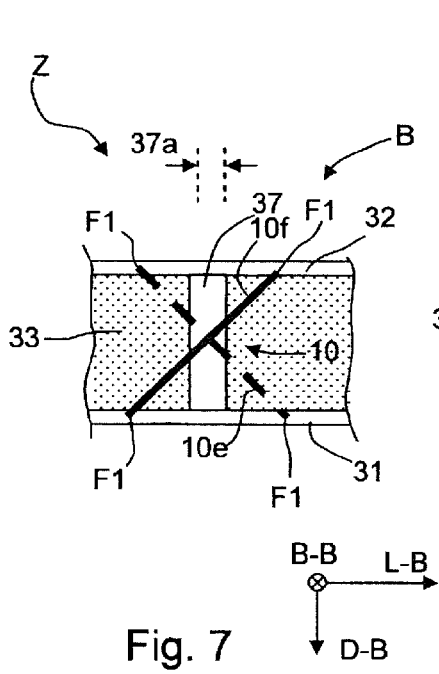

A multitude of reinforcement devices 10 according to an embodiment of the invention can be arranged on such reinforcement regions 37. FIG. 7 shows an exemplary embodiment in which an arrangement or a pair of reinforcement components 10 or 10e, 10f in an X-shaped arrangement project through a core layer reinforcement region 37, wherein in each case a centre section of a reinforcement component 10e, 10f is situated within the core-layer reinforcement region 17. In FIG. 7 the two reinforcement components of an X-shaped arrangement of said reinforcement components are designated by reference characters 10e and 10f. In particular, it can be provided that a multitude of X-shaped arrangements of reinforcement components 10 in the longitudinal direction of the core-layer reinforcement region 37 are arranged one behind the other as a reference longitudinal direction, and following on from each other or resting against each other and/or spaced apart from each other.

Figure 8:
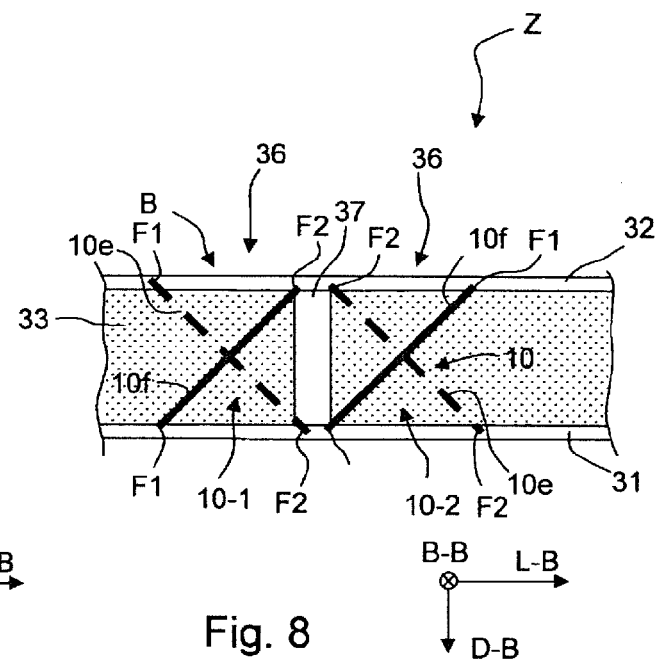

As an alternative or in addition to the above, according to the invention it can be provided that along the longitudinal direction L-R of the rib arrangement and along the longitudinal direction of the core-layer reinforcement region 37, X-shaped arrangements 10-1, 10-2 that are arranged one behind the other are arranged, wherein on both sides of the core-layer reinforcement region 37, X-shaped arrangements 10-1, 10-2 that are situated one behind the other are arranged. FIG. 8 shows an exemplary embodiment in which in the same position, in the longitudinal direction of the core-layer reinforcement region 17 and opposite each other relative to the aforesaid in each case an X-shaped arrangement or a pair 10-1, 10-2 of reinforcement components 10 is arranged. In the herein designated "X-shaped" arrangement of reinforcement components the latter are, in particular, spaced apart from each other in the respective reference longitudinal direction so that in FIGS. 7 and 8 and in FIGS. 9, 10a and 10b one of the reinforcement devices of the respectively-shown pair of reinforcement devices comprises a dashed line in order to indicate that this reinforcement device is situated behind the respective drawing plane. In FIG. 8 the two reinforcement components of an X-shaped arrangement of said reinforcement components are designated by the reference characters 10e and 10f. In the illustration of FIG. 8 the longitudinal direction of the core-layer reinforcement region 37 extends from the viewer of FIG. 8 perpendicularly into the plane of the drawing, with a first X-shaped arrangement 10-1 being situated on the left-hand side, and a second X-shaped arrangement 10-2 being situated on the right-hand side of the core-layer reinforcement region 37. In the exemplary embodiment shown, the ends of the reinforcement components, which ends in each case are situated on the core-layer reinforcement region 37, project through a region of the core-layer reinforcement region 37. As an alternative, the reinforcement components of an X-shaped arrangement of reinforcement components can also be situated beside, i.e. at a distance from, the reinforcement region. In an exemplary embodiment the outer ends, which face the core-layer reinforcement region 37, are situated at a distance of at the maximum the single thickness of the skin shell B at this position. In a variant of these exemplary embodiments the X-shaped arrangements 10-1, 10-2 can alternately be situated on the one side and on the other, opposite, side of the core-layer reinforcement region 37 when viewed in the longitudinal direction of the core-layer reinforcement region 37.

In particular, in an X-shaped arrangement in each case of two reinforcement components it can, in particular, be provided that the two reinforcement components 10, 10f rest against each other or that the two reinforcement components 10e, 10f are interconnected at their respective middle sections. Thus, for example, one of the reinforcement components 10e, 10f can comprise a receiving device, for example a hole, by means of which the respective second reinforcement component is received. In this arrangement the connection of the two reinforcement components 10e, 10f can be provided in such a manner that they are nonrotationally interconnected in order to, in particular, take up any shear stress occurring in the thrust-load-absorbing core layer 13 and/or to stop or prevent any cracks occurring therein. The exemplary embodiments, described with reference to FIGS. 7 and 8, of the invention, result in any damage to the thrust-load-absorbing core layer 13, if such damage occurs on a first side of the sides of the core-layer reinforcement region 37, being unable to migrate through the core-layer reinforcement region 37 to a second side, which is situated opposite the first side.

Generally speaking, the arrangement and/or design of the reinforcement devices for the various aspects of the invention can be identical. Generally speaking, it can be provided that at least part of the reinforcement devices 10; 10a, 10b, 10c, 10d; 10e, 10f are arranged in the end region 56 of the core layer in such a manner that their ends F1 in each case project through the inner skin section 11 and/or the outer skin section 12 at least in part, as shown in FIGS. 5a, 5b, 7, 8, 9, 10a, 10b and 11. The inner skin section 11 or 51 (FIGS. 6 to 10) and/or the outer skin section 12 or 52 (FIGS. 6 to 10) can in each case comprise several skin layers (not shown in the figures). In this arrangement it can, in particular, be provided that at least part of the reinforcement devices 10a, 10b, 10c, 10d are arranged in the skin shell B in such a manner that their ends F1 in each case at least in part project through the inner skin section 11 or 51 and/or the outer skin section 12 or 52.

As an alternative or in addition, it can be provided that several reinforcement components 10; 10a, 10b, 10c, 10d; 10e, 10f in each case at least in part project through the reinforcement region 37. In this arrangement it can, in particular, be provided that in each case one end F2 of a reinforcement component projects through the reinforcement region 37 or has been inserted in said reinforcement region 37 (FIGS. 4, 5 and 8).

Figure 9:
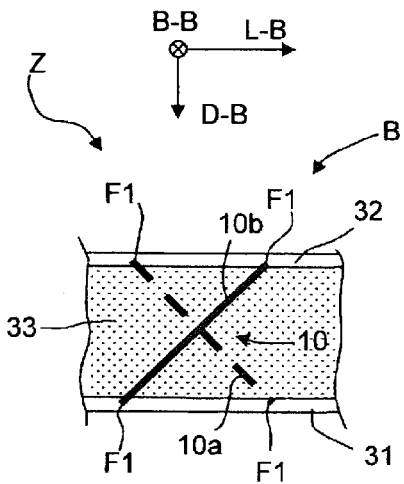
Figure 10A:
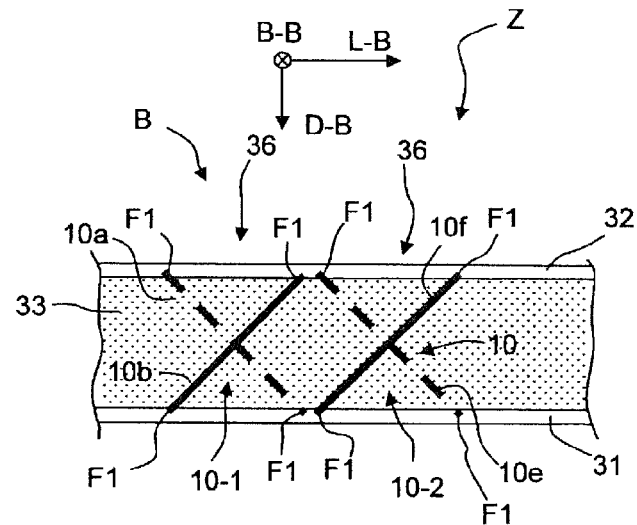
Figure 10B:
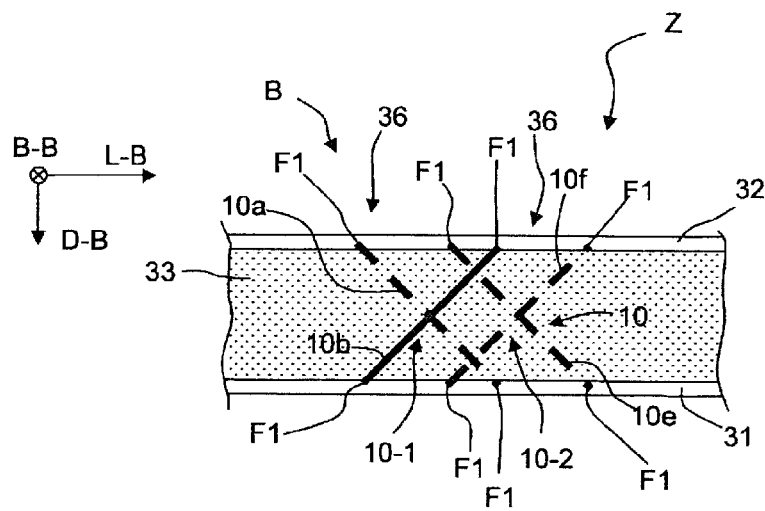

As shown in FIGS. 9, 10a and 10b, in the skin shell B with or without a reinforcement region 37 along a reference longitudinal direction a multitude of reinforcement devices can be arranged, wherein each reinforcement device can be formed from a group of reinforcement components 10a, 10b which, in particular, comprise an X-shaped arrangement. In this arrangement a multitude of pairs of reinforcement components, arranged in an X-shaped manner, can be arranged one behind the other in the reference longitudinal direction (FIG. 9). As shown in FIGS. 10a and 10b, it is also possible for several rows of such reinforcement devices 10 to be arranged, wherein the rows of reinforcement devices are arranged one beside the other when viewed across the reference longitudinal direction. FIG. 10b shows that rows, arranged one beside the other, of reinforcement devices 10-1, 10-2 can be designed in such a manner that the longitudinal extensions of reinforcement components whose ends converge overlap when viewed in the reference longitudinal direct ion.

According to one aspect of the invention a flow body with a structural component according to one of the described embodiments is provided. According to the invention the structural component is a main-load bearing structural part and thus the skin shell and the rib arrangement are main-load bearing structural components.

Figure 6A:
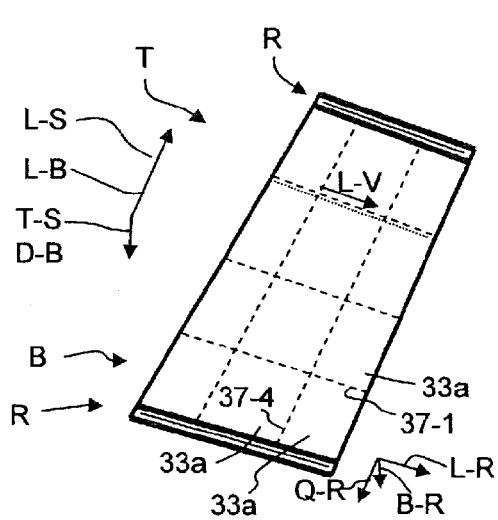
Figure 6B:
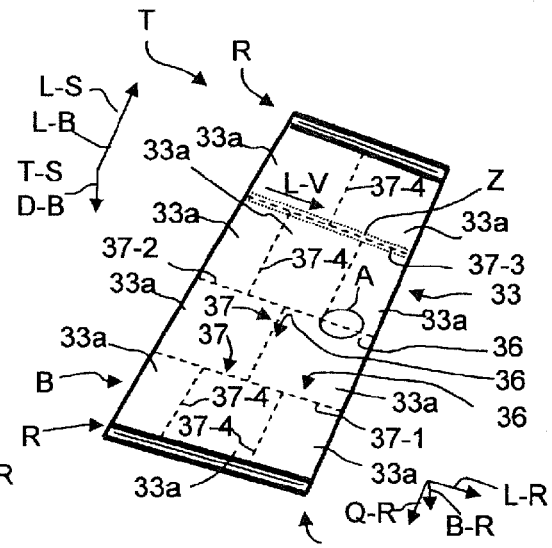

A further aspect of the invention relates to the region of the skin shell B, which region two-dimensionally extends between rib arrangements R, and below is described with reference to the exemplary embodiment shown in FIGS. 6a and 6b. Accordingly, a structural component 1 of a flow body with at least one skin shell B to form a flow surface on the outside of the structural component 1 and a support structure T for attachment of the respective skin shell B are provided, wherein the skin shell B—as described above is described with reference to FIGS. 1 to 5—is constructed as a sandwich and comprises an inner skin section 31, an outer skin section 32 and a thrust-load-absorbing core layer 33 or a foam layer situated between the aforesaid, which skin section two-dimensionally interconnects the inner and the outer skin sections 31, 32 (FIGS. 7, 8). In this arrangement the thrust-load-absorbing core layer 33, which extends between the support components T and the rib arrangement R and which is situated between the inner and the outer skin sections 31, 32, comprises several thrust-load-absorbing core-layer sections 33a that in the longitudinal extension of the thrust-load-absorbing core layer 33 or the foam layer are arranged one beside the other. The thrust-load-absorbing core-layer sections 33a on the contacting sides are interconnected by a core-layer reinforcement region 37 that in its longitudinal direction L-V (FIGS. 6a, 6b) extends across the longitudinal extension of the thrust-load-absorbing core layer 33 through said core-layer reinforcement region 37.

The extension of the core-layer reinforcement regions 37 in the longitudinal extension of the skin shell B and thus of the core-layer sections 33a can be provided in various ways. Corresponding to the course of the core-layer reinforcement regions 37 in the longitudinal extension of the skin shell B, in the embodiment according to FIG. 6a the core-layer sections 33a are arranged in a chess-board-like manner, and in the embodiment according to FIG. 6b are arranged in a longitudinal direction so as to be offset to each other when compared to a chess-board-like arrangement. Generally speaking, the core-layer reinforcement regions 37 extend in such a manner, when viewed in the longitudinal extension of the skin shell B, that they impinge a lateral edge or a corner of core-layer sections 33a that are provided in the shape of rectangular parallelepipeds.

In this arrangement the core-layer reinforcement region 37 can extend between the inner skin section 31 and the outer skin section 32. In this arrangement it can, in particular, be provided that the core-layer reinforcement region 37 is connected to the inner skin section 31 and to the outer skin section 32 so that the core layer reinforcement region 37 is connected to the inner skin section 31 and to the outer skin section 32. The core layer reinforcement region 37 can comprise, in particular, a material that provides at least twice the stiffness of the core-layer reinforcement region 37. According to one embodiment of the skin shell B, the thickness 17a of the core-layer reinforcement region 37 is between 0.1- and 2.0-times the width of the skin shell B at this position, wherein the thickness is measured perpendicularly to the longitudinal extension of the skin shell.

The core-layer reinforcement region 37 can, in particular, comprise resin. FIG. 6 shows an exemplary embodiment of the structural component according to the invention, wherein dashed lines indicate the edge lines of the individual thrust-load-absorbing core-layer sections 33a or the course of the core-layer reinforcement regions 37.

In this context the support structure T can comprise, in particular, at least two support components 5, 6 (not shown in FIG. 6) in each case extending along a longitudinal direction L-S of the structural component 1, and at least one rib arrangement R, connected to the skin shell B, for two-dimensionally supporting the skin shell B on the support structure T (FIGS. 1a, 1b).

The rib arrangement R can, in particular, be T-shaped with regard to its cross section. An exemplary embodiment of a rib arrangement R according to the invention is shown in FIG. 2 and comprises: a rib 21 and a flange component 22 following on from said rib 21, which flange component 22 is connected to a surface region of the skin shell B and is attached to said surface region. The length of the flange component 22 extends in a longitudinal direction L-R of the rib arrangement, and the width of the flange component 22 extends in a transverse direction Q-R of the rib arrangement, wherein the rib 21 protrudes from the flange component 22 in a width direction B-R of the rib arrangement, which width direction is oriented perpendicularly to the longitudinal direction L-R of the rib arrangement and to the transverse direction Q-R of the rib arrangement (FIG. 3).

The support components 5, 6 can, in particular, be designed according to exemplary embodiments that have been described with reference to FIGS. 1 and 2.

In the embodiment of the structural component according to FIG. 6 the courses of the core-layer reinforcement regions 37 are provided in such a manner that rectangular thrust-load-absorbing core-layer sections 33a result. In this arrangement several core-layer reinforcement regions 37-1, 37-2, 37-3 are provided which, in particular, can extend along the longitudinal direction L-R of the rib arrangement. In terms of the notion "along", in this arrangement, in particular, it can be provided that between the orientation of the core-layer reinforcement regions 37-1, 37-2, 37-3, which extend in the longitudinal direction L-R of the rib arrangement, a local angle deviation of at the maximum 30 degrees relative to the orientation of the local longitudinal direction L-R of the rib arrangement or of the longitudinal direction of the rib arrangement R occurs. The core-layer reinforcement regions 37 can be curved or straight. In FIG. 5 the thrust-load-absorbing longitudinal direction L-V of the core layer has been entered, as an example, only in relation to one core layer reinforcement region 37. Furthermore, core-layer reinforcement regions 37-4 are provided which extend across the core-layer reinforcement regions 37-1, 37-2, 37-3 that extend in the longitudinal direction L-R of the rib arrangement.

According to one exemplary embodiment of the structural component according to the invention, it is provided that in the thrust-load-absorbing core layer 33 along a surrounding region Z of a multitude of core-layer reinforcement regions 37 of the skin shell B reinforcement devices according to the invention are integrated (in FIG. 6, for example, such a surrounding region or intermediate region comprises the reference character Z). In this arrangement the reinforcement components and/or reinforcement devices 10 in the longitudinal direction L-V of the core layer of the reinforcement region or along the longitudinal direction of the intermediate region Z are arranged one behind the other. In this arrangement, in a skin shell B which, for example, extends in each case between two rib arrangements R, it can be provided that along and on both sides of the core-layer reinforcement regions 37, which extend therein, reinforcement devices 10 are integrated in the thrust-load-absorbing core layer 33 of the skin shell B. Generally speaking, the surrounding region Z for the arrangement of the reinforcement devices 10 on both sides of the core-layer reinforcement region 37 can extend along its longitudinal extension and up to a distance of a maximum of twice the thickness of the skin shell B on the respective position of the core-layer reinforcement region 37.

The reinforcement devices 10 together with the core layer reinforcement region 33 can be integrated in the skin shell B, as described above with reference to FIGS. 2 and 3, so that identical reference characters are used for components with a similar function. In FIGS. 6 and 7 two embodiments of reinforcement devices 10 arranged beside and along core-layer reinforcement regions 37 are shown. The embodiments of the reinforcement devices 10 and their arrangement, shown in FIGS. 7 and 8, have been implemented analogously to those of the reinforcement devices 10 and their arrangement shown in FIG. 2 or 3. The design and arrangement of the reinforcement devices 10 or of the reinforcement components can be provided as described with reference to the embodiments of FIGS. 3 and 4.

In this context, according to the invention it can, in particular, be provided that several reinforcement components 10, which have been constructed according to one embodiment of the invention, and which are situated one behind the other along the longitudinal direction L-V of the reinforcement region, in each case project through the core layer reinforcement region 37. FIG. 8 shows an exemplary embodiment in which an arrangement or a pair of reinforcement components 10e, 10f in an X-shaped arrangement project through a core layer reinforcement region 37, wherein in each case a centre section of a reinforcement component 10 is situated within the core-layer reinforcement region 37. As an alternative or in addition, reinforcement components 10 can also be situated beside the core layer reinforcement region 37 when viewed in the reinforcement region longitudinal direction L-V of the core layer. In FIGS. 7 and 8 the two reinforcement components of an X-shaped arrangement of said reinforcement components are designated by the reference characters 10e and 10f. In particular, it can be provided that a multitude of X-shaped arrangements of reinforcement components 10 are arranged one behind the other in the longitudinal direction of the core-layer reinforcement region 17, and following on from each other and/or spaced apart from each other.

As an alternative or in addition to the above, according to the invention it can be provided that along the longitudinal direction L-R of the rib arrangement and along the longitudinal direction of the core-layer reinforcement region 37, X-shaped arrangements 10-1, 10-2 that are arranged one behind the other are arranged, wherein, on both sides of the core-layer reinforcement region 37, X-shaped arrangements 10-1, 10-2 that are situated one behind the other are arranged. FIG. 8 shows an exemplary embodiment in which in the same position, in the longitudinal direction of the core-layer reinforcement region 37 and opposite each other relative to each other in each case an X-shaped arrangement or a pair 10-1, 10-2 of reinforcement components 10 is arranged. In FIG. 8 the two reinforcement components of an X-shaped arrangement of said reinforcement components are designated by the reference characters 10e and 10f. In the illustration of FIG. 8 the longitudinal direction L-V of the core-layer reinforcement region 17 extends from the viewer of FIG. 6 perpendicularly into the plane of the drawing, with a first X-shaped arrangement 10-1 being situated on the left-hand side, and a second X-shaped arrangement 10-2 being situated on the right-hand side of the core-layer reinforcement region 37. In the exemplary embodiment shown, the ends of the reinforcement components, which ends in each case are situated on the core-layer reinforcement region 37 of the reinforcement components, project through a region of the core-layer reinforcement region 37. As an alternative, the reinforcement components of an X-shaped arrangement of reinforcement components can also be situated beside, i.e. at a distance from, the reinforcement region. In an exemplary embodiment the outer ends, which face the core-layer reinforcement region 37, are situated at a distance of at the maximum the thickness of the skin shell B at this position. In a variant of these exemplary embodiments the X-shaped arrangements 10-1, 10-2 can alternately be situated on the one side and on the other, opposite, side of the core-layer reinforcement region 37 when viewed in the longitudinal direction of the core-layer reinforcement region 37.

The exemplary embodiments of the invention, which exemplary embodiments have been described with reference to FIGS. 7 to 10b, result in any damage to the thrust-load-absorbing core layer 33, if such damage occurs on a first side of the core-layer reinforcement region 37, being unable to migrate through the core-layer reinforcement region 37 to a second side, which is situated opposite the first side.

A further aspect of the invention refers to a main-load bearing skin shell B for a structural component 1, which skin shell B in its two-dimensionally extending inside region 50 is constructed as a sandwich component in such a manner as described above with reference to FIGS. 1 to 5 and 5 to 7. This aspect of the invention is described below with reference to FIGS. 9 and 10 which in the inside region 50 of the skin shell B show: the skin shell B, constructed as a sandwich component, with an inner skin section 51, an outer skin section 52 and a thrust-load-absorbing core layer 53, situated between the aforesaid, which two-dimensionally interconnects the inner 51 and the outer 52 skin sections. The characteristics of these structural components are as described above. In the illustration of FIGS. 9 and 10 some constituent parts and components of the embodiment shown in each case comprise reference characters that are identical to those used in previous figures with reference to the particular functionalities or characteristics.

The skin shell B is designed for being affixed to a support component with an outer edge section 60 with an outer edge 61 that comprises: a connection region 63 that does not comprise a core layer, which connection region 63 extends along the edge 61 with the inner skin section 51 and the outer skin section 52 and a monolithic intermediate layer 65 situated between said skin sections 51, 52. In the outer edge section 60 a transition region 62 is provided in which, when viewed from the inside region 50, the thrust-load-absorbing core layer 63 ends, i.e. in which transition region 62 the outer edge 55 of the thrust-load-absorbing core layer 53 is situated or extends. A comparison of FIGS. 8 and 9 shows that the edge 61 or the edge 55 extends along the longitudinal direction L-S of the structural component 1, and the connection region 63 extends from the inside region 50 to the width direction B-S of the structural component 1. In the transition region 62 a region 66 can be provided in which the thickness of the monolithic intermediate layer tapers in the direction of the outer edge 61 to reduce the cross-sectional thickness of the skin shell.

According to the invention, it is provided that in an end region 56 of the core layer along the outer edge section 60 of the skin shell B reinforcement devices 10 are integrated that project through the thrust-load-absorbing core layer 53.

The reinforcement device can be designed as described with reference to FIGS. 4 and 5 or 7 and 8. In this arrangement, in particular, an X-arrangement of reinforcement components 10e, 10f can be used. In FIG. 9 two X-arrangements 10-1 and 10-2, which are arranged one behind the other in the width direction B-S of the structural component 1, are arranged. Generally speaking, when viewed in the width direction B-S of the structural component 1, at least one reinforcement component 10 and, in particular, at least one X-arrangement of reinforcement components 10 can be arranged. Preferably, in the longitudinal direction L-S of the structural component 1, in other words along the edge 55 of the thrust-load-absorbing core layer 33, several reinforcement devices 10 or 10-1 and/or 10-2 are arranged.

As an alternative or in addition to the above, according to the invention it can be provided that along the longitudinal direction L-R of the rib arrangement and along the longitudinal direction of the core-layer reinforcement region 17, X-shaped arrangements 10-1, 10-2 that are arranged one behind the other are arranged, wherein, on both sides of the core-layer reinforcement region 17, X-shaped arrangements 10-1, 10-2 that are situated one behind the other are arranged. FIG. 5 shows an exemplary embodiment in which in the same position, in the longitudinal direction of the core-layer reinforcement region 17 and opposite each other relative to the aforesaid in each case an X-shaped arrangement or a pair 10-1, 10-2 of reinforcement components 10 is arranged. In FIG. 5 the two reinforcement components of an X-shaped arrangement of said components are designated by the reference characters 10e and 10f. In the illustration of FIG. 9 the longitudinal direction of the core-layer reinforcement region 17 extends from the viewer of FIG. 9 perpendicularly into the plane of the drawing, with a first X-shaped arrangement 10-1 being situated on the left-hand side, and a second X-shaped arrangement 10-2 being situated on the right-hand side of the core-layer reinforcement region 17. In the exemplary embodiment shown, the ends of the reinforcement components, which ends in each case are situated on the core-layer reinforcement region 17 of the reinforcement components, project through a region of the core-layer reinforcement region 17. As an alternative, the reinforcement components of an X-shaped arrangement of reinforcement components can also be situated beside, i.e. at a distance from, the reinforcement region. In an exemplary embodiment the outer ends, which face the core-layer reinforcement region 17, are situated at a distance of at the maximum the thickness of the skin shell B at this position. In a variant of these exemplary embodiments the X-shaped arrangements 10-1, 10-2 can alternately be situated on the one side and on the other, opposite, side of the core-layer reinforcement region 17 when viewed in the longitudinal direction of the core-layer reinforcement region 17.

In an X-shaped arrangement in each case of two reinforcement components it can, in particular, be provided that the two reinforcement components 10e, 10f rest against each other or that the two reinforcement components 10e, 10f are interconnected at their respective middle sections. Thus, for example, one of the reinforcement components 10e, 10f can comprise a receiving device, for example a hole, by means of which the respective second reinforcement component is received. In this arrangement the connection of the two reinforcement components 10e, 10f can be provided in such a manner that they are nonrotationally interconnected in order to, in particular, take up any shear stress occurring in the thrust-load-absorbing core layer.

The exemplary embodiments of the invention, which embodiments have been described with reference to FIGS. 3a and 4a, 3c result in any damage to the thrust-load-absorbing core layer 13, if such damage occurs on a first side of the core-layer reinforcement region 17, being unable to migrate through the core-layer reinforcement region 17 to a second side, which is situated opposite the first side.

The skin shell B according to this aspect of the invention can, in particular, be received by a support structure T and can be affixed to said support structure T as described in FIGS. 1a, 1b and 2 or FIGS. 5a, 5b, 5c. In this aspect of the invention it can, in particular, also be provided that the skin shell B extends between support components 5, 6 and the rib arrangement R, as has been described above with reference to FIGS. 1a and 1b. Optionally, as an alternative or in addition, it can be provided that the thrust-load-absorbing core layer 53 comprises several thrust-load-absorbing core-layer sections (not shown in FIG. 9 or 10) arranged one beside the other in the longitudinal extension of the thrust-load-absorbing core layer 53, as has been described with reference to FIGS. 3 to 8. In this arrangement, as described with reference to FIG. 6, the thrust-load-absorbing core-layer sections in each case on the contacting sides are interconnected by a core layer reinforcement region 37 that extends in the longitudinal direction L-V of the reinforcement region across the longitudinal extension of the thrust-load-absorbing core layer 33 or 63 through said core layer reinforcement region 37.

According to the invention, it can, furthermore, be provided that, when viewed from the inside region 60 in front of the thrust-load-absorbing connection region 63 that does not comprise a core layer, an intermediate region 62 is provided in which the thickness of the thrust-load-absorbing core layer 53 continuously decreases in the direction of the edge 55 while forming a wedge-shaped section of the monolithic intermediate layer 65 at least between the side of the thrust-load-absorbing core layer 53, which side faces the outer skin section 52, and the outer skin section 52 or between the side of the thrust-load-absorbing core layer 53, which side faces the inner skin section 51, and the inner skin section 51. In this exemplary embodiment it can, in particular, be provided that in an end region 56 of the core layer along the outer edge section 30 of the skin shell B reinforcement devices 10; 10e, 10f according to a herein described exemplary embodiment are integrated, which reinforcement devices 10; 10e, 10f project through the thrust-load-absorbing core layer and partly through the two wedge-shaped sections of the monolithic intermediate layer 65.

The end region 56 of the core layer for the arrangement of the reinforcement devices can extend from the edge of the end of the core layer to a distance of a maximum of four times the thickness of the skin shell B at the edge of the end of the core layer.

Generally speaking, the arrangement and/or design of the reinforcement components and/or reinforcement devices for the various aspects of the invention can be identical.

The invention claimed is:
1. A structural component comprising:
   at least one main-load bearing skin shell formed as a sandwich from an inner skin section, an outer skin section, and a core layer which is disposed therebetween and which connects the inner and the outer skin section in a laminar manner; and
   a support structure for fixing the skin shell, wherein the support structure is formed of a first portion consisting of at least two support components and a second portion consisting of a plate-shaped connection piece which extends between and across the support components and is connected with the skin shell along a reference longitudinal direction;
   wherein the plate-shaped connection piece is disposed at the support structure outside the support components for supporting the skin shell and connected to the inner skin section adjacent to the inner skin section, wherein the plate-shaped connection piece comprises a connecting region of the inner skin section of the skin shell that covers the plate-shaped connection piece of the support structure, in which a plurality of reinforcement components are integrated along the reference longitudinal direction and extend through the core layer in a thickness direction of the core layer;

wherein in the skin shell at least one profile carrier is disposed which extends along the reference longitudinal direction for forming a reinforcement section in the connecting region of the plate-shaped connection piece;

wherein the at least one profile carrier is connected to the inner skin section and outer skin section for stabilization of the skin shell in case of damage of the skin shell and which thereby supports the inner skin section and outer skin section with regard to each other from the outside;

wherein the plurality of reinforcement components are exclusively provided in the connecting region and in an intermediate region of the skin shell, the intermediate region being disposed outside of the connecting region and extending in an area from an edge of the lateral end of the connecting region of the skin shell to a distance of a maximum of ten times a thickness of the skin shell; and wherein each of the plurality of reinforcement components at least in part comprises one of a pin-shaped design or a needle-shaped design.

2. The structural component according to claim 1, wherein at least some of the reinforcement components are disposed in the core layer such that the inner ends thereof at least partially penetrate at least the inner skin section and/or the outer skin section, wherein the inner skin section and the outer skin section each comprise several layers and at least a part of the reinforcement components penetrate at least a first layer.

3. The structural component according to claim 1, wherein the support structure comprises:

at least one rib arrangement which extends between and across the support components and is connected with the skin shell along the reference longitudinal direction for supporting the skin shell to the support structure in a laminar manner, the plate-shaped connection piece which extends in the longitudinal direction of the rib arrangement and which is formed as a flange component, connected with the connecting region of the inner skin section of the skin shell; and a rib which follows on from the flange component and protrudes from the skin shell in a reference longitudinal direction of the rib arrangement.

4. The structural component according to claim 1, wherein the plate-shaped connection piece for connecting the same with the skin shell is in a laminar manner bonded to the inner skin section due to an adhesive or is connected thereto by fasteners.

5. The structural component according to claim 1, wherein the reinforcement components are integrated in the intermediate region of the skin shell along the reference longitudinal direction.

6. The structural component according to claim 1, wherein several of the reinforcement components are disposed beside each other in an area across a longitudinal direction of a rib arrangement, and several of the reinforcement components are disposed along reinforcement profiles and along the longitudinal direction of the rib arrangement.

7. The structural component according to claim 1, further comprising at least one reinforcement profile carrier, which is formed of two profile plates and a support rib that connects the aforesaid, wherein one of the profile plates is connected to the inner skin section and the respective other one of the profile plates is connected to the outer skin section, such that a profile cross section of the reinforcement profile carrier is a double-T profile cross section.

8. The structural component according to claim 7, wherein at edge portions which define the connecting region, two of the reinforcement profile carriers are disposed side by side, between which the reinforcement components are inserted in the core layer.

9. The structural component according to claim 8, wherein the reinforcement components are inserted such that ends of a respective one of the reinforcement components at least partially penetrate the profile plate being disposed at the inner skin section and the profile plate being disposed at the outer skin section, the profile plates being part of the reinforcement profile carriers which lay side by side to each other.

10. The structural component according to claim 1, further comprising at least one reinforcement profile carrier, which is formed of two profile plates and two support ribs, wherein one of the two profile plates is connected to the inner skin section and the other one of the two profile plates is connected to the outer skin section, such that a profile cross section of the reinforcement profile carrier is a box-shaped profile cross section.

11. The structural component according to claim 10, wherein the reinforcement components are inserted such that ends of a respective one of the reinforcement components at least partially penetrate the profile plate being disposed at the inner skin section and the profile plate being disposed at the outer skin section, the profile plates being part of the same reinforcement profile carrier.

12. The structural component according to claim 1, wherein along at least one reinforcement profile carrier in a longitudinal direction of a rib arrangement several of the reinforcement components are integrated which project through at least 85% of the core layer in the thickness direction of the core layer in order to improve crack resistance of the skin shell in an outer edge section.

13. The structural component according to claim 1, wherein the reinforcement components are arranged into groups in a volume component of the skin shell, wherein each volume component is arranged one behind the other along a longitudinal direction of a rib, and wherein each volume component comprises a combination of at least two of the reinforcement components whose alignments each deviate by a maximum of 30 degrees from a thickness direction of the skin shell, and which are arranged in a regular or irregular manner around a centre axis of the volume component.

14. The structural component according to claim 13, wherein the reinforcement components are arranged into pairs that comprise X-shaped orientations when viewed in a direction of a longitudinal extension of an outer edge section of the skin shell.

15. The structural component according to claim 1, wherein an angle between the longitudinal direction of the respective reinforcement component and a thickness direction of the skin shell at this position is within a range of between 45 degrees and 10 degrees.

16. The structural component according to claim 1, wherein the reinforcement components at least in part comprise the pin-shaped design.

17. The structural component according to claim 16, wherein one end of each of the reinforcement components comprises a foot-like widened part.

18. The structural component according to claim 1, wherein the reinforcement components comprise the needle-shaped design.

19. The structural component according to claim 1, wherein the core layer comprises a reinforcement region which extends in a first intermediate region lying along a longitudinal direction of a rib arrangement and across a longitudinal direction of the connecting region of the core layer, wherein the reinforcement region comprises a material that provides at least twice a stiffness of the core layer.

20. The structural component according to claim 19, wherein the core-layer reinforcement region comprises resin.

21. The structural component according to claim 19, wherein several of the reinforcement components at least in part project through the reinforcement region.

22. A flow body with a structural component with a main-load bearing skin shell according to claim 1, wherein the main-load bearing skin shell comprises a skin of the flow body.

* * * * *